(12) United States Patent
Kapadia et al.

(10) Patent No.: US 12,740,839 B2
(45) Date of Patent: Sep. 22, 2026

(54) STERILE INTERFACE MODULE FOR ROBOTIC SURGICAL ASSEMBLIES

(71) Applicant: Covidien LP, Mansfield, MA (US)

(72) Inventors: Jaimeen Kapadia, Cambridge, MA (US); Brock Kopp, Colorado Springs, CO (US); Mark H. MacLeod, Southbury, CT (US); Chi Min Seow, Watertown, MA (US); Michael Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 85 days.

(21) Appl. No.: 18/976,196

(22) Filed: Dec. 10, 2024

(65) Prior Publication Data

US 2025/0099192 A1 Mar. 27, 2025

Related U.S. Application Data

(63) Continuation of application No. 16/960,599, filed as application No. PCT/US2019/012472 on Jan. 7, 2019, now Pat. No. 12,193,774.

(Continued)

(51) Int. Cl.
*A61B 34/35* (2016.01)
*A61B 34/30* (2016.01)
(Continued)

(52) U.S. Cl.
CPC .............. *A61B 34/35* (2016.02); *A61B 90/96* (2016.02); *A61B 2034/302* (2016.02); *A61B 2090/0813* (2016.02)

(58) Field of Classification Search
CPC ......... A61B 34/35; A61B 34/30; A61B 34/37; A61B 90/08; A61B 90/96; A61B 90/98;
(Continued)

(56) References Cited

U.S. PATENT DOCUMENTS 2,957,353 A 10/1960 Babacz
3,111,328 A 11/1963 Di Rito et al.
(Continued)

FOREIGN PATENT DOCUMENTS

CA 2451558 A1 1/2003
CN 1547454 A 11/2004
(Continued)

OTHER PUBLICATIONS

Chinese Office Action (with English translation), dated Nov. 4, 2019, corresponding to counterpart Chinese Application No. 201780002103.3; 20 total pages.

(Continued)

*Primary Examiner* — Sarah A Long
(74) *Attorney, Agent, or Firm* — Carter, DeLuca & Farrell, LLP

(57) ABSTRACT

The sterile interface module includes a body member for coupling a surgical instrument to a robotic surgical assembly, a decoupling collar supported on the body member and movable relative to the body member from a first position to a second position, and a drive transfer assembly supported by the body member. The drive transfer assembly includes a drive coupler and a transfer shaft extending from the drive coupler. The drive coupler engages the robotic surgical assembly and the transfer shaft engages the surgical instrument. The drive coupler engages the robotic surgical assembly while the decoupling collar is in the first position to enable the robotic surgical assembly to robotically control the surgical instrument. The drive coupler is retracted within the body member while the decoupling collar is in the second position to prevent the drive coupler from engaging the robotic surgical assembly.

20 Claims, 26 Drawing Sheets

Related U.S. Application Data

(60) Provisional application No. 62/615,060, filed on Jan. 9, 2018.

(51) Int. Cl.
*A61B 90/96* (2016.01)
*A61B 90/00* (2016.01)

(58) Field of Classification Search
CPC .......... A61B 90/90; A61B 2017/00482; A61B 2034/302; A61B 2090/0813
See application file for complete search history.

(56) References Cited

U.S. PATENT DOCUMENTS 3,695,058 A 10/1972 Keith, Jr.
3,734,515 A 5/1973 Dudek
3,759,336 A 9/1973 Marcovitz et al.
4,162,399 A 7/1979 Hudson
4,606,343 A 8/1986 Conta et al.
4,683,772 A 8/1987 Colimitra
4,705,038 A 11/1987 Sjostrom et al.
4,722,685 A 2/1988 de Estrada et al.
4,823,807 A 4/1989 Russell et al.
4,862,759 A 9/1989 Trevelyan et al.
4,874,181 A 10/1989 Hsu
5,129,118 A 7/1992 Walmesley
5,129,570 A 7/1992 Schulze et al.
5,152,744 A 10/1992 Krause
5,301,061 A 4/1994 Nakada et al.
5,312,023 A 5/1994 Green et al.
5,326,013 A 7/1994 Green et al.
5,350,355 A 9/1994 Sklar
5,383,874 A 1/1995 Jackson et al.
5,383,880 A 1/1995 Hooven
5,389,098 A 2/1995 Tsuruta et al.
5,395,033 A 3/1995 Byrne et al.
5,400,267 A 3/1995 Denen et al.
5,411,508 A 5/1995 Bessler et al.
5,413,267 A 5/1995 Solyntjes et al.
5,427,087 A 6/1995 Ito et al.
5,433,721 A 7/1995 Hooven et al.
5,467,911 A 11/1995 Tsuruta et al.
5,476,379 A 12/1995 Disel
5,487,499 A 1/1996 Sorrentino et al.
5,518,163 A 5/1996 Hooven
5,518,164 A 5/1996 Hooven
5,526,822 A 6/1996 Burbank et al.
5,529,235 A 6/1996 Boiarski et al.
5,535,934 A 7/1996 Boiarski et al.
5,535,937 A 7/1996 Boiarski et al.
5,540,375 A 7/1996 Bolanos et al.
5,540,706 A 7/1996 Aust et al.
5,542,594 A 8/1996 McKean et al.
5,549,637 A 8/1996 Crainich
5,553,675 A 9/1996 Pitzen et al.
5,562,239 A 10/1996 Boiarski et al.
5,564,615 A 10/1996 Bishop et al.
5,609,560 A 3/1997 Ichikawa et al.
5,626,587 A 5/1997 Bishop et al.
5,632,432 A 5/1997 Schulze et al.
5,645,209 A 7/1997 Green et al.
5,647,526 A 7/1997 Green et al.
5,653,374 A 8/1997 Young et al.
5,658,300 A 8/1997 Bito et al.
5,662,662 A 9/1997 Bishop et al.
5,667,517 A 9/1997 Hooven
5,693,042 A 12/1997 Boiarski et al.
5,704,534 A 1/1998 Huitema et al.
5,713,505 A 2/1998 Huitema
5,762,603 A 6/1998 Thompson
5,779,130 A 7/1998 Alesi et al.
5,782,396 A 7/1998 Mastri et al.
5,782,397 A 7/1998 Koukline
5,784,542 A 7/1998 Ohm et al.
5,792,573 A 8/1998 Pitzen et al.
5,797,536 A 8/1998 Smith et al.
5,797,900 A 8/1998 Madhani et al.
5,820,009 A 10/1998 Melling et al.
5,863,159 A 1/1999 Lasko
5,908,427 A 6/1999 McKean et al.
5,954,259 A 9/1999 Viola et al.
5,964,774 A 10/1999 McKean et al.
5,993,454 A 11/1999 Longo
6,010,054 A 1/2000 Johnson et al.
6,017,354 A 1/2000 Culp et al.
6,032,849 A 3/2000 Mastri et al.
6,045,560 A 4/2000 McKean et al.
6,090,123 A 7/2000 Culp et al.
6,126,651 A 10/2000 Mayer
6,129,547 A 10/2000 Cise et al.
6,165,169 A 12/2000 Panescu et al.
6,239,732 B1 5/2001 Cusey
6,241,139 B1 6/2001 Milliman et al.
6,264,086 B1 7/2001 McGuckin, Jr.
6,264,087 B1 7/2001 Whitman
6,302,311 B1 10/2001 Adams et al.
6,315,184 B1 11/2001 Whitman
6,321,855 B1 11/2001 Barnes
6,329,778 B1 12/2001 Culp et al.
6,343,731 B1 2/2002 Adams et al.
6,348,061 B1 2/2002 Whitman
6,368,324 B1 4/2002 Dinger et al.
6,371,909 B1 4/2002 Hoeg et al.
6,434,507 B1 8/2002 Clayton et al.
6,443,973 B1 9/2002 Whitman
6,451,027 B1 9/2002 Cooper et al.
6,461,372 B1 10/2002 Jensen et al.
6,488,197 B1 12/2002 Whitman
6,491,201 B1 12/2002 Whitman
6,533,157 B1 3/2003 Whitman
6,537,280 B2 3/2003 Dinger et al.
6,554,844 B2 4/2003 Lee et al.
6,610,066 B2 8/2003 Dinger et al.
6,611,793 B1 8/2003 Burnside et al.
6,645,218 B1 11/2003 Cassidy et al.
6,654,999 B2 12/2003 Stoddard et al.
6,698,643 B2 3/2004 Whitman
6,699,177 B1 3/2004 Wang et al.
6,716,233 B1 4/2004 Whitman
6,743,240 B2 6/2004 Smith et al.
6,783,533 B2 8/2004 Green et al.
6,792,390 B1 9/2004 Burnside et al.
6,793,652 B1 9/2004 Whitman et al.
6,817,508 B1 11/2004 Racenet et al.
6,830,174 B2 12/2004 Hillstead et al.
6,846,308 B2 1/2005 Whitman et al.
6,846,309 B2 1/2005 Whitman et al.
6,849,071 B2 2/2005 Whitman et al.
6,860,892 B1 3/2005 Tanaka et al.
6,899,538 B2 5/2005 Matoba
6,905,057 B2 6/2005 Swayze et al.
6,959,852 B2 11/2005 Shelton, IV et al.
6,964,363 B2 11/2005 Wales et al.
6,981,628 B2 1/2006 Wales
6,981,941 B2 1/2006 Whitman et al.
6,986,451 B1 1/2006 Mastri et al.
6,988,649 B2 1/2006 Shelton, IV et al.
7,032,798 B2 4/2006 Whitman et al.
RE39,152 E 6/2006 Aust et al.
7,055,731 B2 6/2006 Shelton, IV et al.
7,059,508 B2 6/2006 Shelton, IV et al.
7,077,856 B2 7/2006 Whitman
7,111,769 B2 9/2006 Wales et al.
7,122,029 B2 10/2006 Koop et al.
7,140,528 B2 11/2006 Shelton, IV
7,141,049 B2 11/2006 Stern et al.
7,143,923 B2 12/2006 Shelton, IV et al.
7,143,925 B2 12/2006 Shelton, IV et al.
7,143,926 B2 12/2006 Shelton, IV et al.
7,147,138 B2 12/2006 Shelton, IV
7,172,104 B2 2/2007 Scirica et al.
7,225,964 B2 6/2007 Mastri et al.
7,238,021 B1 7/2007 Johnson

(56) References Cited

U.S. PATENT DOCUMENTS 7,246,734 B2 7/2007 Shelton, IV
7,252,660 B2 8/2007 Kunz
7,328,828 B2 2/2008 Ortiz et al.
7,364,061 B2 4/2008 Swayze et al.
7,380,695 B2 6/2008 Doll et al.
7,380,696 B2 6/2008 Shelton, IV et al.
7,404,508 B2 7/2008 Smith et al.
7,407,078 B2 8/2008 Shelton, IV et al.
7,416,101 B2 8/2008 Shelton, IV et al.
7,419,080 B2 9/2008 Smith et al.
7,422,139 B2 9/2008 Shelton, IV et al.
7,422,592 B2 9/2008 Morley et al.
7,431,189 B2 10/2008 Shelton, IV et al.
7,441,684 B2 10/2008 Shelton, IV et al.
7,448,525 B2 11/2008 Shelton, IV et al.
7,464,846 B2 12/2008 Shelton, IV et al.
7,464,847 B2 12/2008 Viola et al.
7,464,849 B2 12/2008 Shelton, IV et al.
7,481,347 B2 1/2009 Roy
7,481,824 B2 1/2009 Boudreaux et al.
7,487,899 B2 2/2009 Shelton, IV et al.
7,549,564 B2 6/2009 Boudreaux
7,565,993 B2 7/2009 Milliman et al.
7,568,603 B2 8/2009 Shelton, IV et al.
7,575,144 B2 8/2009 Ortiz et al.
7,588,175 B2 9/2009 Timm et al.
7,588,176 B2 9/2009 Timm et al.
7,637,409 B2 12/2009 Marczyk
7,641,093 B2 1/2010 Doll et al.
7,644,848 B2 1/2010 Swayze et al.
7,670,334 B2 3/2010 Hueil et al.
7,673,780 B2 3/2010 Shelton, IV et al.
7,699,835 B2 4/2010 Lee et al.
7,721,931 B2 5/2010 Shelton, IV et al.
7,738,971 B2 6/2010 Swayze et al.
7,740,159 B2 6/2010 Shelton, IV et al.
7,743,960 B2 6/2010 Whitman et al.
7,758,613 B2 7/2010 Whitman
7,766,210 B2 8/2010 Shelton, IV et al.
7,770,773 B2 8/2010 Whitman et al.
7,770,775 B2 8/2010 Shelton, IV et al.
7,793,812 B2 9/2010 Moore et al.
7,799,039 B2 9/2010 Shelton, IV et al.
7,802,712 B2 9/2010 Milliman et al.
7,803,151 B2 9/2010 Whitman
7,822,458 B2 10/2010 Webster, III et al.
7,845,534 B2 12/2010 Viola et al.
7,845,537 B2 12/2010 Shelton, IV et al.
7,857,185 B2 12/2010 Swayze et al.
7,870,989 B2 1/2011 Viola et al.
7,900,805 B2 3/2011 Shelton, IV et al.
7,905,897 B2 3/2011 Whitman et al.
7,918,230 B2 4/2011 Whitman et al.
7,922,061 B2 4/2011 Shelton, IV et al.
7,922,719 B2 4/2011 Ralph et al.
7,947,034 B2 5/2011 Whitman
7,951,071 B2 5/2011 Whitman et al.
7,954,682 B2 6/2011 Giordano et al.
7,959,051 B2 6/2011 Smith et al.
7,963,433 B2 6/2011 Whitman et al.
7,967,178 B2 6/2011 Scirica et al.
7,967,179 B2 6/2011 Olson et al.
7,992,758 B2 8/2011 Whitman et al.
8,011,550 B2 9/2011 Aranyi et al.
8,016,178 B2 9/2011 Olson et al.
8,016,855 B2 9/2011 Whitman et al.
8,020,743 B2 9/2011 Shelton, IV
8,025,199 B2 9/2011 Whitman et al.
8,035,487 B2 10/2011 Malackowski
8,052,024 B2 11/2011 Viola et al.
8,074,859 B2 12/2011 Kostrzewski
8,092,451 B2 1/2012 Schechter et al.
8,114,118 B2 2/2012 Knodel et al.
8,127,975 B2 3/2012 Olson et al.
8,132,705 B2 3/2012 Viola et al.
8,152,516 B2 4/2012 Harvey et al.
8,157,150 B2 4/2012 Viola et al.
8,157,151 B2 4/2012 Ingmanson et al.
8,182,494 B1 5/2012 Yencho et al.
8,186,555 B2 5/2012 Shelton, IV et al.
8,186,587 B2 5/2012 Zmood et al.
8,220,367 B2 7/2012 Hsu
8,235,273 B2 8/2012 Olson et al.
8,237,388 B2 8/2012 Jinno et al.
8,241,322 B2 8/2012 Whitman et al.
8,272,554 B2 9/2012 Whitman et al.
8,292,150 B2 10/2012 Bryant
8,292,888 B2 10/2012 Whitman
8,342,379 B2 1/2013 Whitman et al.
8,348,130 B2 1/2013 Shah et al.
8,348,855 B2 1/2013 Hillely et al.
8,353,440 B2 1/2013 Whitman et al.
8,357,144 B2 1/2013 Whitman et al.
8,365,633 B2 2/2013 Simaan et al.
8,365,972 B2 2/2013 Aranyi et al.
8,371,492 B2 2/2013 Aranyi et al.
8,372,057 B2 2/2013 Cude et al.
8,391,957 B2 3/2013 Carlson et al.
8,403,926 B2 3/2013 Nobis et al.
8,418,904 B2 4/2013 Wenchell et al.
8,424,739 B2 4/2013 Racenet et al.
8,454,585 B2 6/2013 Whitman
8,465,476 B2 6/2013 Rogers et al.
8,505,802 B2 8/2013 Viola et al.
8,517,241 B2 8/2013 Nicholas et al.
8,523,043 B2 9/2013 Ullrich et al.
8,551,076 B2 10/2013 Duval et al.
8,561,871 B2 10/2013 Rajappa et al.
8,561,874 B2 10/2013 Scirica
8,602,287 B2 12/2013 Yates et al.
8,623,000 B2 1/2014 Humayun et al.
8,627,995 B2 1/2014 Smith et al.
8,632,463 B2 1/2014 Drinan et al.
8,636,192 B2 1/2014 Farascioni et al.
8,636,766 B2 1/2014 Milliman et al.
8,647,258 B2 2/2014 Aranyi et al.
8,652,121 B2 2/2014 Quick et al.
8,657,174 B2 2/2014 Yates et al.
8,657,177 B2 2/2014 Scirica et al.
8,672,206 B2 3/2014 Aranyi et al.
8,696,552 B2 4/2014 Whitman
8,708,213 B2 4/2014 Shelton, IV et al.
8,715,306 B2 5/2014 Faller et al.
8,758,391 B2 6/2014 Swayze et al.
8,806,973 B2 8/2014 Ross et al.
8,808,311 B2 8/2014 Heinrich et al.
8,820,605 B2 9/2014 Shelton, IV
8,851,355 B2 10/2014 Aranyi et al.
8,858,571 B2 10/2014 Shelton, IV et al.
8,875,972 B2 11/2014 Weisenburgh, II et al.
8,888,762 B2 11/2014 Whitman
8,893,946 B2 11/2014 Boudreaux et al.
8,899,462 B2 12/2014 Kostrzewski et al.
8,905,289 B2 12/2014 Patel et al.
8,919,630 B2 12/2014 Milliman
8,925,786 B2 1/2015 Holsten et al.
8,931,680 B2 1/2015 Milliman
8,939,344 B2 1/2015 Olson et al.
8,950,646 B2 2/2015 Viola
8,960,519 B2 2/2015 Whitman et al.
8,961,396 B2 2/2015 Azarbarzin et al.
8,967,443 B2 3/2015 McCuen
8,968,276 B2 3/2015 Zemlok et al.
8,968,337 B2 3/2015 Whitfield et al.
8,992,422 B2 3/2015 Spivey et al.
9,016,545 B2 4/2015 Aranyi et al.
9,023,014 B2 5/2015 Chowaniec et al.
9,033,868 B2 5/2015 Whitman et al.
9,055,943 B2 6/2015 Zemlok et al.
9,064,653 B2 6/2015 Prest et al.
9,072,515 B2 7/2015 Hall et al.
9,113,847 B2 8/2015 Whitman et al.
9,113,875 B2 8/2015 Viola et al.
9,113,876 B2 8/2015 Zemlok et al.

(56) References Cited

U.S. PATENT DOCUMENTS 9,113,899 B2 8/2015 Garrison et al.
9,216,013 B2 12/2015 Scirica et al.
9,241,712 B2 1/2016 Zemlok et al.
9,282,961 B2 3/2016 Whitman et al.
9,282,963 B2 3/2016 Bryant
9,295,522 B2 3/2016 Kostrzewski
9,307,986 B2 4/2016 Hall et al.
9,937,626 B2 4/2018 Rockrohr
10,179,413 B2 1/2019 Rockrohr
10,245,096 B2 4/2019 Trivedi
12,193,774 B2 1/2025 Kapadia et al.
2001/0031975 A1 10/2001 Whitman
2002/0040217 A1 4/2002 Jinno
2002/0049454 A1 4/2002 Whitman et al.
2002/0082479 A1 6/2002 Frangesch et al.
2002/0165541 A1 11/2002 Whitman
2003/0038938 A1 2/2003 Jung et al.
2003/0165794 A1 9/2003 Matoba
2004/0034369 A1 2/2004 Sauer et al.
2004/0111012 A1 6/2004 Whitman
2004/0133189 A1 7/2004 Sakurai
2004/0153124 A1 8/2004 Whitman
2004/0176751 A1 9/2004 Weitzner et al.
2004/0193146 A1 9/2004 Lee et al.
2005/0125027 A1 6/2005 Knodel et al.
2005/0131442 A1 6/2005 Yachia et al.
2006/0079884 A1 4/2006 Manzo
2006/0142656 A1 6/2006 Malackowski et al.
2006/0142740 A1 6/2006 Sherman et al.
2006/0142744 A1 6/2006 Boutoussov
2006/0235436 A1 10/2006 Anderson
2006/0259073 A1 11/2006 Miyamoto et al.
2006/0278680 A1 12/2006 Viola
2006/0284730 A1 12/2006 Schmid et al.
2007/0023476 A1 2/2007 Whitman et al.
2007/0023477 A1 2/2007 Whitman et al.
2007/0029363 A1 2/2007 Popov
2007/0084897 A1 4/2007 Shelton et al.
2007/0102472 A1 5/2007 Shelton
2007/0152014 A1 7/2007 Gillum et al.
2007/0175947 A1 8/2007 Ortiz et al.
2007/0175949 A1 8/2007 Shelton et al.
2007/0175950 A1 8/2007 Shelton, IV et al.
2007/0175951 A1 8/2007 Shelton et al.
2007/0175955 A1 8/2007 Shelton et al.
2007/0270784 A1 11/2007 Smith et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0039256 A1 2/2008 Jinno et al.
2008/0058801 A1 3/2008 Taylor et al.
2008/0103491 A1 5/2008 Omori et al.
2008/0109012 A1 5/2008 Falco et al.
2008/0110958 A1 5/2008 McKenna et al.
2008/0119870 A1 5/2008 Williams
2008/0147089 A1 6/2008 Loh et al.
2008/0167736 A1 7/2008 Swayze et al.
2008/0185419 A1 8/2008 Smith et al.
2008/0188841 A1 8/2008 Tomasello et al.
2008/0197167 A1 8/2008 Viola et al.
2008/0208195 A1 8/2008 Shores et al.
2008/0237296 A1 10/2008 Boudreaux et al.
2008/0245175 A1 10/2008 Jinno et al.
2008/0251561 A1 10/2008 Eades et al.
2008/0255413 A1 10/2008 Zemlok et al.
2008/0255607 A1 10/2008 Zemlok
2008/0262654 A1 10/2008 Omori et al.
2008/0308603 A1 12/2008 Shelton et al.
2009/0012533 A1 1/2009 Barbagli et al.
2009/0090763 A1 4/2009 Zemlok et al.
2009/0099876 A1 4/2009 Whitman
2009/0138006 A1 5/2009 Bales et al.
2009/0171147 A1 7/2009 Lee et al.
2009/0182193 A1 7/2009 Whitman et al.
2009/0209946 A1 8/2009 Swayze et al.
2009/0209990 A1 8/2009 Yates et al.
2009/0254094 A1 10/2009 Knapp et al.
2009/0299141 A1 12/2009 Downey et al.
2010/0016852 A1 1/2010 Manzo et al.
2010/0016853 A1 1/2010 Burbank
2010/0023022 A1 1/2010 Zeiner et al.
2010/0069942 A1 3/2010 Shelton, IV
2010/0193568 A1 8/2010 Scheib et al.
2010/0211053 A1 8/2010 Ross et al.
2010/0225073 A1 9/2010 Porter et al.
2010/0228264 A1 9/2010 Robinson et al.
2010/0292708 A1 11/2010 Madhani et al.
2011/0071508 A1 3/2011 Duval et al.
2011/0077673 A1 3/2011 Grubac et al.
2011/0121049 A1 5/2011 Malinouskas et al.
2011/0125138 A1 5/2011 Malinouskas et al.
2011/0139851 A1 6/2011 McCuen
2011/0155783 A1 6/2011 Rajappa et al.
2011/0155786 A1 6/2011 Shelton, IV
2011/0172648 A1 7/2011 Jeong
2011/0174009 A1 7/2011 Iizuka et al.
2011/0174099 A1 7/2011 Ross et al.
2011/0184245 A1 7/2011 Xia et al.
2011/0204119 A1 8/2011 McCuen
2011/0218522 A1 9/2011 Whitman
2011/0276057 A1 11/2011 Conlon et al.
2011/0290854 A1 12/2011 Timm et al.
2011/0295242 A1 12/2011 Spivey et al.
2011/0295269 A1 12/2011 Swensgard et al.
2012/0000962 A1 1/2012 Racenet et al.
2012/0010616 A1 1/2012 Huang et al.
2012/0059360 A1 3/2012 Namiki
2012/0074199 A1 3/2012 Olson et al.
2012/0080475 A1 4/2012 Smith et al.
2012/0080485 A1 4/2012 Woodard, Jr. et al.
2012/0089131 A1 4/2012 Zemlok et al.
2012/0104071 A1 5/2012 Bryant
2012/0116368 A1 5/2012 Viola
2012/0116416 A1 5/2012 Neff et al.
2012/0143002 A1 6/2012 Aranyi et al.
2012/0168485 A1 7/2012 Marczyk et al.
2012/0172924 A1 7/2012 Allen, IV
2012/0199630 A1 8/2012 Shelton, IV
2012/0223121 A1 9/2012 Viola et al.
2012/0245428 A1 9/2012 Smith et al.
2012/0253329 A1 10/2012 Zemlok et al.
2012/0310220 A1 12/2012 Malkowski et al.
2012/0323226 A1 12/2012 Chowaniec et al.
2012/0330285 A1 12/2012 Hartoumbekis et al.
2013/0020376 A1 1/2013 Shelton, IV et al.
2013/0032629 A1 2/2013 Viola
2013/0093149 A1 4/2013 Saur et al.
2013/0131695 A1 5/2013 Scarfogliero et al.
2013/0158542 A1 6/2013 Manzo et al.
2013/0181035 A1 7/2013 Milliman
2013/0184704 A1 7/2013 Beardsley et al.
2013/0214025 A1 8/2013 Zemlok et al.
2013/0274722 A1 10/2013 Kostrzewski et al.
2013/0282052 A1 10/2013 Aranyi et al.
2013/0292451 A1 11/2013 Viola et al.
2013/0313304 A1 11/2013 Shelton, IV et al.
2013/0317486 A1 11/2013 Nicholas et al.
2013/0319706 A1 12/2013 Nicholas et al.
2013/0324978 A1 12/2013 Nicholas et al.
2013/0324979 A1 12/2013 Nicholas et al.
2013/0325095 A1 12/2013 Ollivier
2013/0331858 A1 12/2013 Devengenzo et al.
2013/0334281 A1 12/2013 Williams
2014/0005640 A1 1/2014 Shelton, IV et al.
2014/0012236 A1 1/2014 Williams et al.
2014/0012237 A1 1/2014 Pribanic et al.
2014/0012289 A1 1/2014 Snow et al.
2014/0025046 A1 1/2014 Williams et al.
2014/0039343 A1* 2/2014 Mescher ................ A61B 90/98
600/562
2014/0110455 A1 4/2014 Ingmanson et al.
2014/0148821 A1 5/2014 Nakayama
2014/0166023 A1 6/2014 Kishi

(56) References Cited

U.S. PATENT DOCUMENTS

| | | | |
|---|---|---|---|
| 2014/0207125 | A1 | 7/2014 | Applegate et al. |
| 2014/0207182 | A1 | 7/2014 | Zergiebel et al. |
| 2014/0207185 | A1 | 7/2014 | Goble et al. |
| 2014/0236174 | A1 | 8/2014 | Williams et al. |
| 2014/0276932 | A1 | 9/2014 | Williams et al. |
| 2014/0299647 | A1 | 10/2014 | Scirica et al. |
| 2014/0303668 | A1 | 10/2014 | Nicholas et al. |
| 2014/0358129 | A1 | 12/2014 | Zergiebel et al. |
| 2014/0361068 | A1 | 12/2014 | Aranyi et al. |
| 2014/0365235 | A1 | 12/2014 | DeBoer et al. |
| 2014/0373652 | A1 | 12/2014 | Zergiebel et al. |
| 2014/0378761 | A1 | 12/2014 | Zorn et al. |
| 2015/0014392 | A1 | 1/2015 | Williams et al. |
| 2015/0048144 | A1 | 2/2015 | Whitman |
| 2015/0076205 | A1 | 3/2015 | Zergiebel |
| 2015/0080912 | A1 | 3/2015 | Sapre |
| 2015/0112381 | A1 | 4/2015 | Richard |
| 2015/0122870 | A1 | 5/2015 | Zemlok et al. |
| 2015/0133224 | A1 | 5/2015 | Whitman et al. |
| 2015/0150547 | A1 | 6/2015 | Ingmanson et al. |
| 2015/0150574 | A1 | 6/2015 | Richard et al. |
| 2015/0157320 | A1 | 6/2015 | Zergiebel et al. |
| 2015/0157321 | A1 | 6/2015 | Zergiebel et al. |
| 2015/0164502 | A1 | 6/2015 | Richard et al. |
| 2015/0201931 | A1 | 7/2015 | Zergiebel et al. |
| 2015/0272577 | A1 | 10/2015 | Zemlok et al. |
| 2015/0297199 | A1 | 10/2015 | Nicholas et al. |
| 2015/0303996 | A1 | 10/2015 | Calderoni |
| 2015/0320420 | A1 | 11/2015 | Penna et al. |
| 2015/0327850 | A1 | 11/2015 | Kostrzewski |
| 2015/0342601 | A1 | 12/2015 | Williams et al. |
| 2015/0342603 | A1 | 12/2015 | Zergiebel et al. |
| 2015/0374366 | A1 | 12/2015 | Zergiebel et al. |
| 2015/0374370 | A1 | 12/2015 | Zergiebel et al. |
| 2015/0374371 | A1 | 12/2015 | Richard et al. |
| 2015/0374372 | A1 | 12/2015 | Zergiebel et al. |
| 2015/0374449 | A1 | 12/2015 | Chowaniec et al. |
| 2015/0380187 | A1 | 12/2015 | Zergiebel et al. |
| 2016/0038013 | A1 | 2/2016 | Czupalla et al. |
| 2016/0095585 | A1 | 4/2016 | Zergiebel et al. |
| 2016/0095596 | A1 | 4/2016 | Scirica et al. |
| 2016/0106406 | A1 | 4/2016 | Cabrera |
| 2016/0113648 | A1 | 4/2016 | Zergiebel et al. |
| 2016/0113649 | A1 | 4/2016 | Zergiebel et al. |
| 2016/0242861 | A1 | 8/2016 | Flatt et al. |
| 2018/0110572 | A1* | 4/2018 | Flatt .................... A61B 17/162 |
| 2018/0168748 | A1 | 6/2018 | Kapadia |

FOREIGN PATENT DOCUMENTS

| | | | | |
|---|---|---|---|---|
| CN | 1957854 | A | 5/2007 | |
| CN | 101495046 | A | 7/2009 | |
| CN | 102247182 | A | 11/2011 | |
| CN | 103732174 | A | 4/2014 | |
| CN | 105611894 | A | 5/2016 | |
| DE | 102008053842 | A1 | 5/2010 | |
| EP | 0443576 | A1 | 8/1991 | |
| EP | 0705571 | A1 | 4/1996 | |
| EP | 1563793 | A1 | 8/2005 | |
| EP | 1769754 | A1 | 4/2007 | |
| EP | 2316345 | A1 | 5/2011 | |
| EP | 2668910 | A2 | 12/2013 | |
| EP | 3416582 | A1 | 12/2018 | |
| ES | 2333509 | A1 | 2/2010 | |
| JP | 2005125075 | A | 5/2005 | |
| JP | 2016533816 | A | 11/2016 | |
| KR | 20120022521 | A | 3/2012 | |
| NO | 2017210516 | | 12/2017 | |
| WO | 2011016640 | A2 | 2/2011 | |
| WO | 2011108840 | A2 | 9/2011 | |
| WO | 2012040984 | A1 | 4/2012 | |
| WO | 2015088647 | A1 | 6/2015 | |
| WO | 2016043845 | A1 | 3/2016 | |
| WO | 2017202831 | A1 | 11/2017 | |
| WO | 2017205308 | A1 | 11/2017 | |
| WO | WO-2017205311 | A1 * | 11/2017 | ............ A61B 34/71 |
| WO | 2018217430 | A1 | 11/2018 | |

OTHER PUBLICATIONS

European Search Report, dated Dec. 20, 2019, corresponding to counterpart European Application No. 17803383.3; 11 pages.

European Communication dated Jan. 30, 2020 and European Communication dated Jan. 13, 2020 with Supplementary European Search Report, corresponding to counterpart European Application No. 17803386.6; 4 total pages.

European Search Report, dated Dec. 20, 2019, corresponding to counterpart European Application No. 17803381.7; 11 pages.

European Communication dated Jan. 24, 2020, corresponding to counterpart European Application No. 17803384.1; 1 page.

European Search Report dated Jan. 3, 2020, corresponding to counterpart European Application No. 17803397.3; 7 pages.

Extended European Search Report dated Feb. 6, 2020 corresponding to counterpart Patent Application EP 17803392.4.

Extended EP Search Report for application No. 22193394.8 dated Nov. 30, 2022.

Extended European Search Report corresponding to International Application No. EP 14 18 4882.0 dated May 12, 2015.

Canadian Office Action corresponding to International Application No. CA 2640399 dated May 7, 2015.

Japanese Office Action corresponding to International Application No. JP 2011-084092 mailed May 20, 2015.

Partial European Search Report corresponding to International Application No. EP 14 19 6704.2 dated May 11, 2015.

Chinese Office Action (with English translation), dated May 8, 2020, corresponding to counterpart Chinese Application No. 201780002103.3; 21 total pages.

India Examination Report for application No. 202017030960 dated May 23, 2021 with English translation.

Chinese Office Action for Application No. 2019800075460 dated Feb. 14, 2023 with English translation.

Japanese Office Action for Application No. 2020-537661 dated Aug. 4, 2021 with English translation.

Extended European Search Report for application No. 19738140.3 dated Nov. 22, 2021.

Japanese Notice of Allowance for application No. 2020-537661 dated Dec. 22, 2021 with English Translation.

Partial Supplementary European Search Report for application No. 19738140.3 dated Jul. 22, 2021.

Japanese Office Action corresponding to International Application No. JP 2011-197365 mailed Mar. 23, 2015.

Japanese Office Action corresponding to International Application No. JP 2014-148482 mailed Jun. 2, 2015.

Extended European Search Report corresponding to International Application No. EP 14 18 9358.6 dated Jul. 8, 2015.

Extended European Search Report corresponding to International Application No. EP 14 19 6148.2 dated Apr. 23, 2015.

Australian Office Action corresponding to International Application No. AU 2010241367 dated Aug. 20, 2015.

Partial European Search Report corresponding to International Application No. EP 14 19 9783.3 dated Sep. 3, 2015.

Extended European Search Report corresponding to International Application No. EP 15 16 9962.6 dated Sep. 14, 2015.

Extended European Search Report corresponding to International Application No. EP 15 15 1076.5 dated Apr. 22, 2015.

Japanese Office Action corresponding to International Application No. JP 2011-084092 dated Jan. 14, 2016.

Extended European Search Report corresponding to International Application No. EP 12 19 7970.2 dated Jan. 28, 2016.

Chinese Office Action corresponding to International Application No. CN 201210560638.1 dated Oct. 21, 2015.

European Office Action corresponding to International Application No. EP 14 15 9056.2 dated Oct. 26, 2015.

Australian Examination Report No. 1 corresponding to International Application No. AU 2015200153 dated Dec. 11, 2015.

(56) References Cited

OTHER PUBLICATIONS

Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, mailed Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
Chinese First Office Action corresponding to counterpart Chinese Patent Appln. No. CN 2014800674869 dated Jan. 24, 2018.
Extended European Search Report corresponding to counterpart EP Application No. 14 87 0110.5 dated Mar. 20, 2018.
Chinese Second Office Action corresponding to counterpart Patent Appln. CN 2014800674869 dated Aug. 1, 2018.
International Search Report for (PCT/US2014/061863) dated Jan. 21, 2015; 4 pages.

* cited by examiner 352
350
354
356
358b
360
358a

STERILE INTERFACE MODULE FOR ROBOTIC SURGICAL ASSEMBLIES

CROSS-REFERENCE TO RELATED APPLICATIONS

This application is a Continuation Application which claims the benefit of and priority to U.S. application Ser. No. 16/960,599, filed Jul. 8, 2020, which is a U.S. National Stage Application filed under 35 U.S.C. § 371 (a) of International Patent Application Serial No. PCT/US2019/012472, filed Jan. 7, 2019, which claims the benefit of and priority to U.S. Provisional Application Ser. No. 62/615,060, filed on Jan. 9, 2018, the entire disclosure of each of which is incorporated by reference herein.

TECHNICAL FIELD

The present disclosure relates to robotics, and more specifically to robotic surgical devices, assemblies, and/or systems for performing endoscopic surgical procedures and methods of use thereof.

BACKGROUND

Robotic surgical systems have been used in minimally invasive medical procedures. Some robotic surgical systems include a console supporting a surgical robotic arm and a surgical instrument mounted to the robotic arm. The surgical instrument may have an elongated shaft that supports at least one end effector (e.g., forceps or a grasping tool) on a distal end thereof. In some robotic surgical systems, the entire length of the elongated shaft of the surgical instrument must pass through a holder or other feature of the robotic arm, thereby making removal or exchange of the surgical instrument from the robotic arm cumbersome.

Manually-operated surgical instruments often include a handle assembly for actuating the functions of the surgical instrument; however, when using a robotic surgical system, no handle assembly is typically present to actuate the functions of the end effector. It is the robotic arm of the robotic surgical system that provides mechanical power to the surgical instrument for its operation and movement. Each robotic arm may include an instrument drive unit that is operatively connected to the surgical instrument by an interface. The interface couples the selected surgical instrument to the robotic surgical system for driving operations of the surgical instrument and to provide structure for ready removal or exchange of the surgical instrument from the robotic arm.

During a surgical procedure, some portions of the surgical instrument may be exposed to a non-sterile environment or non-sterile components. Such exposure may contaminate the surgical instrument, or portions thereof. Since it is imperative that many of the components of the robotic surgical system remain sterile, there is a need to maintain sterility at the interface used to couple the surgical instrument to the robotic surgical system for protecting sterile components of the robotic surgical system from being contaminated by the non-sterile portions of the surgical instrument. A need also exists for a robotic surgical system that enables more efficient and expeditious removal or exchange of a surgical instrument and which has improved usability.

SUMMARY

In accordance with an aspect of the present disclosure, a sterile interface module for coupling an electromechanical robotic surgical instrument to a robotic surgical assembly is provided. The sterile interface module includes a body member, a decoupling collar, and a drive transfer assembly. The body member may be configured to selectively couple the surgical instrument to the robotic surgical assembly. The decoupling collar may be supported on the body member and may be movable relative to the body member from a first position to a second position. The drive transfer assembly may be supported by the body member and may include a drive coupler and a transfer shaft extending from the drive coupler. The drive coupler may be engagable with the robotic surgical assembly and the transfer shaft may be engagable with the surgical instrument. The drive coupler may be configured to engage the robotic surgical assembly while the decoupling collar is in the first position to enable the robotic surgical assembly to robotically control the surgical instrument. The drive coupler may be retracted within the body member while the decoupling collar is in the second position to prevent the drive coupler from engaging the robotic surgical assembly.

In some embodiments, the sterile interface module may further include a locking plate and a locking tab. The locking plate may be coupled to the decoupling collar. The locking tab may extend from the body member and may be selectively engagable with the locking plate to prevent the decoupling collar from moving from the second position to the first position. The locking plate may be movable with the decoupling collar.

In certain embodiments, the sterile interface module may further include a release ring supported on the body member. The release ring may be positioned to prevent the decoupling collar from moving from the first position to the second position. The release ring may be selectively removable from the body member to enable the decoupling collar to move from the first position to the second position. The release ring may seal the body member.

In some embodiments, the sterile interface module may further include an electrical connector supported on the body member. The electrical connector may be configured to enable electrical communication between the robotic surgical assembly and the surgical instrument. Movement of the decoupling collar from the first position to the second position may prevent the electrical connector from providing electrical communication between the robotic surgical assembly and the surgical instrument. The electrical connector may be recessed within the body member.

In certain embodiments, the body member may define a vent.

In some embodiments, the body member may include a pair of nubs that selectively couple to the robotic surgical assembly to secure the body member to the robotic surgical assembly.

According to yet another aspect of the present disclosure, a robotic surgical system is provided. The robotic surgical system includes a surgical instrument including an end effector, a robotic surgical assembly, and a sterile interface module. The sterile interface module may be positionable between the robotic surgical assembly and the surgical instrument to couple the surgical instrument to the robotic surgical assembly.

In some embodiments, the sterile interface module may include nubs that selectively couple to the robotic surgical assembly to secure the sterile interface module to the robotic surgical assembly. The robotic surgical assembly may include buttons that face in the same direction and are depressible to decouple the nubs of the sterile interface module from the robotic surgical assembly so that the sterile interface module releases from the robotic surgical assembly.

In certain embodiments, the robotic surgical system may include a reset cam supported in the sterile interface module and configured to selectively reset the sterile interface module after the decoupling collar is moved from the first position toward the second position.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Figure 1:
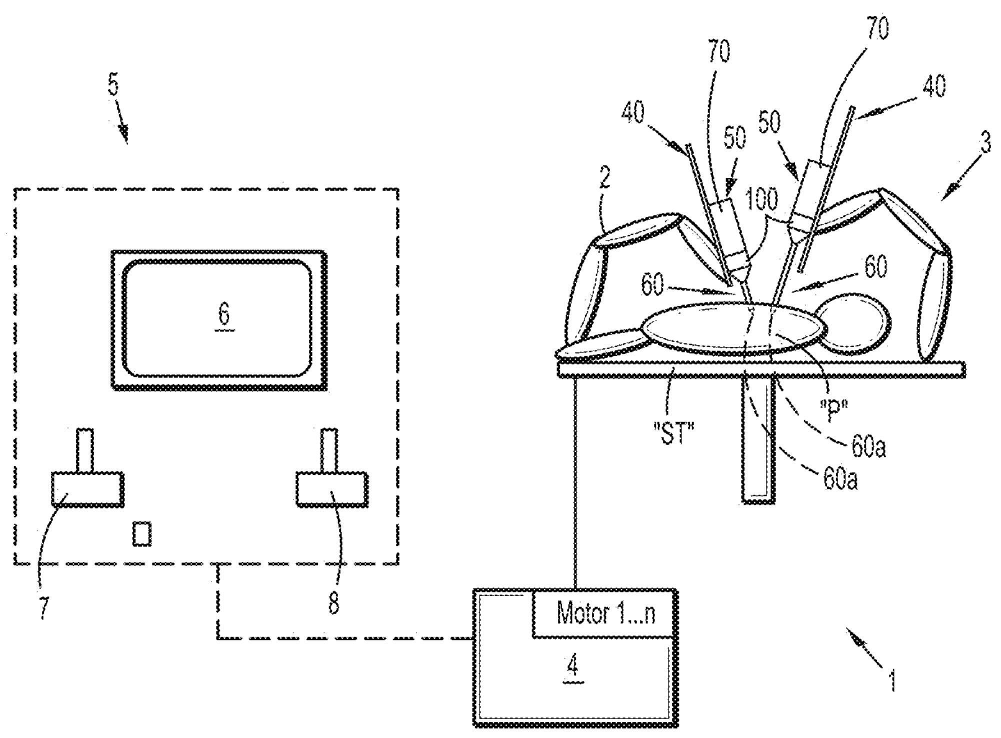
FIG. 1 is a schematic illustration of a robotic surgical system in accordance with the present disclosure.

Embodiments of the present disclosure are described in detail with reference to the drawings, in which like reference numerals designate identical or corresponding elements in each of the several views. As used herein, the term "distal" refers to that portion of the robotic surgical system, surgical assembly, or component thereof, that is closer to a patient, while the term "proximal" refers to that portion of the robotic surgical system, surgical assembly, or component thereof, that is farther from the patient. As used herein, the terms parallel and perpendicular are understood to include relative configurations that are substantially parallel and substantially perpendicular up to about + or −10 degrees from true parallel and true perpendicular.

As used herein, the term "clinician" refers to a doctor, nurse, or other care provider and may include support personnel. In the following description, well-known functions or construction are not described in detail to avoid obscuring the present disclosure in unnecessary detail.

Figure 2:
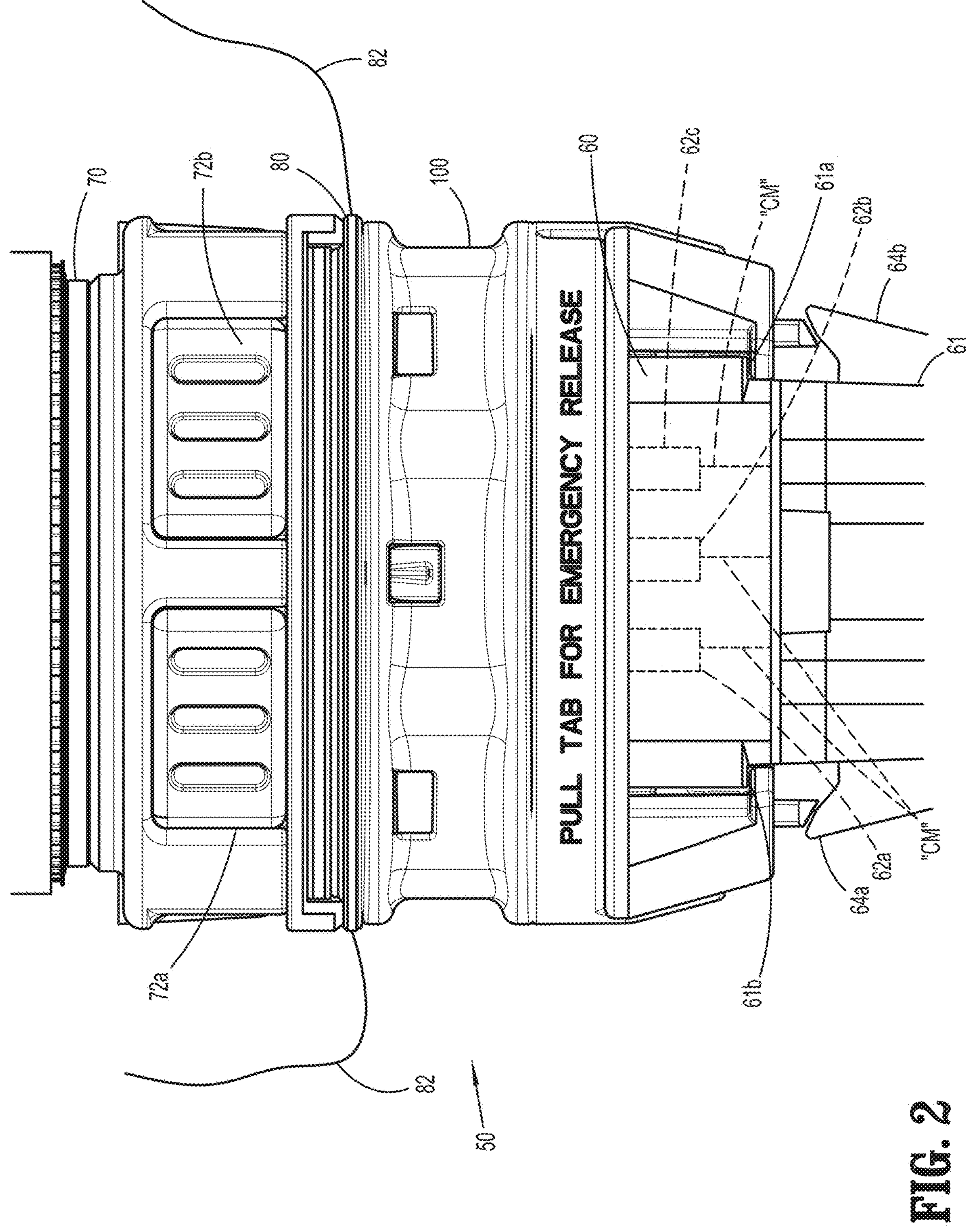
FIG. 2 is a front view of a portion of a robotic surgical assembly of the robotic surgical system of FIG. 1.
Figure 3:
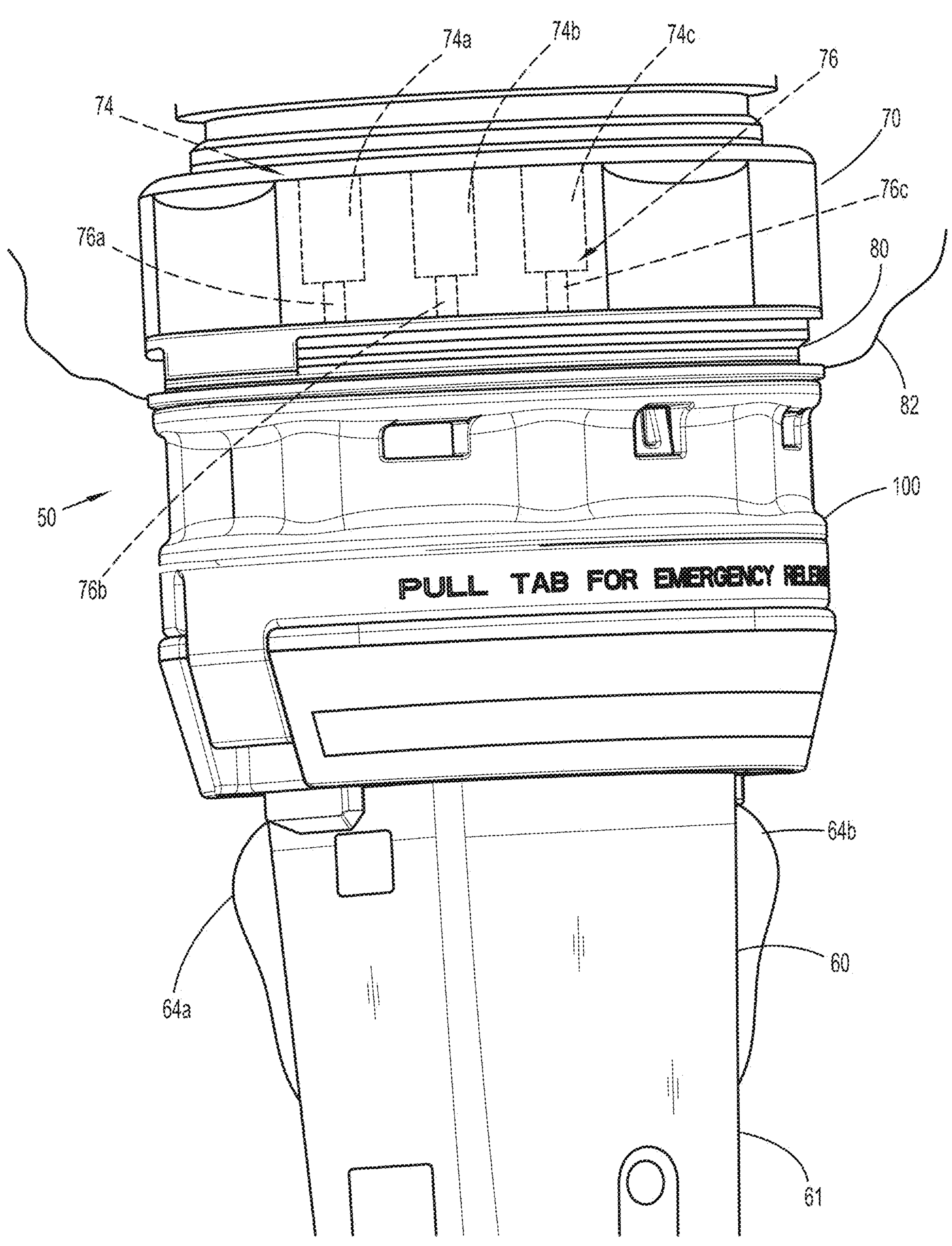
FIG. 3 is a rear view of a portion of the robotic surgical assembly of FIG. 2.

Referring initially to FIGS. 1 to 3, a surgical system, such as, for example, a robotic surgical system 1, generally includes one or more surgical robotic arms 2, 3, a control device 4, and an operating console 5 coupled with control device 4. Any of the surgical robotic arms 2, 3 may have a robotic surgical assembly 50 and an electromechanical surgical instrument 60 coupled thereto. The robotic surgical assembly 50 further includes an instrument drive unit 70 and a collar assembly or sterile interface module 100 that couples the electromechanical surgical instrument 60 to the instrument drive unit 70 as described in greater detail below. In some embodiments, the robotic surgical assembly 50 may be removably attached to a slide rail 40 of one of the surgical robotic arms 2, 3. In certain embodiments, the robotic surgical assembly 50 may be fixedly attached to the slide rail 40 of one of the surgical robotic arms 2, 3.

Operating console 5 includes a display device 6, which is set up to display three-dimensional images; and manual input devices 7, 8, by means of which a clinician (not shown), is able to telemanipulate the robotic arms 2, 3 in a first operating mode, as known in principle to a person skilled in the art. Each of the robotic arms 2, 3 may be composed of any number of members, which may be connected through joints. The robotic arms 2, 3 may be driven by electric drives (not shown) that are connected to control device 4. The control device 4 (e.g., a computer) is set up to activate the drives, for example, by means of a computer program, in such a way that the robotic arms 2, 3, the attached robotic surgical assembly 50, and thus the electromechanical surgical instrument 60 (including an electromechanical end effector 60*a* thereof) execute a desired movement according to a movement defined by means of the manual input devices 7, 8. The control device 4 may also be set up in such a way that it regulates the movement of the robotic arms 2, 3 and/or of the drives.

The robotic surgical system 1 is configured for use on a patient “P” positioned (e.g., lying) on a surgical table “ST” to be treated in a minimally invasive manner by means of a surgical instrument such as the electromechanical surgical instrument 60. The robotic surgical system 1 may also include more than two robotic arms 2, 3, the additional robotic arms likewise connected to the control device 4 and telemanipulatable by means of the operating console 5. A surgical instrument, for example, the electromechanical surgical instrument 60, may also be attached to any additional robotic arm(s).

The control device 4 may control one or more motors, e.g., motors (Motor 1 . . . n), each motor configured to drive movement of the robotic arms 2, 3 in any number of directions. Further, the control device 4 may control the instrument drive unit 70 including a motor assembly 74 thereof that drives various operations of the end effector 60*a* of the electromechanical surgical instrument 60. The motor assembly 74 of the robotic surgical assembly 50 includes any number of motors 74*a*, 74*b*, 74*c*, etc. that couple to the sterile interface module 100 via a corresponding number of motor couplers 76 such as motor couplers 76*a*, 76*b*, 76*c*, etc. extending from the motors 74*a*, 74*b*, 74*c*, etc.

In general, the robotic surgical assembly 50 transfers power and actuation forces (e.g., torque) from the motors 74*a*, 74*b*, 74*c*, etc. of the motor assembly 74, through the sterile interface module 100, to driven members 62*a*, 62*b*, 62*c*, etc. supported within an instrument housing 61 of the electromechanical surgical instrument 60. Such transfer of power and actuation forces ultimately drives movement of components of the end effector 60*a* of the electromechanical surgical instrument 60 for operating the electromechanical surgical instrument 60. This movement may include, for example, a movement of a knife blade (not shown) and/or a closing and opening of jaw members (not shown) of the end effector 60*a*, an articulation/rotation/pitch/yaw of the end effector 60*a*, and/or the actuation or firing of the end effector 60*a* (e.g. a stapling portion of the end effector 60*a*). The driven members 62*a*, 62*b*, 62*c*, etc. of the electromechanical surgical instrument 60 are coupled to one or more coupling members “CM” (e.g., cables, drive rods, etc.) at a first end thereof. The one or more coupling members “CM” of the electromechanical surgical instrument 60 extend along the electromechanical surgical instrument 60 to the end effector 60*a* of the electromechanical surgical instrument 60. A second end of the one or more coupling members “CM” couples to the end effector 60*a* of the electromechanical surgical instrument 60 for operating the end effector 60*a* as detailed above. Reference may be made to commonly owned International Patent Application No. PCT/US14/61329, filed on Oct. 20, 2014 entitled “Wrist and Jaw Assemblies for Robotic Surgical Systems,” U.S. Pat. No. 8,636,192, or U.S. Pat. No. 8,925,786, the entire contents of each of which are incorporated by reference herein, for a detailed discussion of illustrative examples of the construction and operation of end effectors for use with or connection to the electromechanical surgical instrument 60.

The robotic surgical assembly 50 may also be configured for the activation or firing of an electrosurgical energy-based instrument or the like, for example, via a drive mechanism (not shown) that may include, for instance, screws/nuts, cable drives, pulleys, friction wheels, rack and pinion arrangements, etc., or combinations thereof.

For a detailed discussion of the construction and operation of a similar robotic surgical system having one or more of the same or similar components for use with one or more components of the presently described robotic surgical system, reference may be made to U.S. Patent Application Publication No. 2012/0116416, filed on Nov. 3, 2011, entitled “Medical Workstation,” and/or U.S. Patent Application Ser. No. 62/341,714, filed on May 26, 2016, entitled “Robotic Surgical Assemblies,” the entire contents of each of which are incorporated by reference herein.

With reference to FIGS. 2, 3, 4, and 13A-13D, the robotic surgical assembly 50 of the robotic surgical system 1 includes an instrument drive unit or housing 70 supporting the sterile interface module 100 that couples the electromechanical surgical instrument 60 to the instrument drive unit 70. A distal or leading end portion of the instrument drive unit 70 includes a pair of buttons 72*a*, 72*b* supported adjacent to one another and disposed in the same direction (e.g., front or forward-facing). The buttons 72*a*, 72*b*, which are spring biased by one or more springs (not shown) may be simultaneously depressible to attach and/or release the sterile interface module 100 to/from the instrument drive unit 70. Each of the buttons 72*a*, 72*b* may include one or more protuberances 72*c*, 72*d* that are configured to selectively engage with one or more attachment nubs 118*a*-118*d* (described in greater detail below) of the sterile interface module 100 to selectively secure the sterile interface module 100 to the instrument drive unit 70.

Figures 13A, 13B:
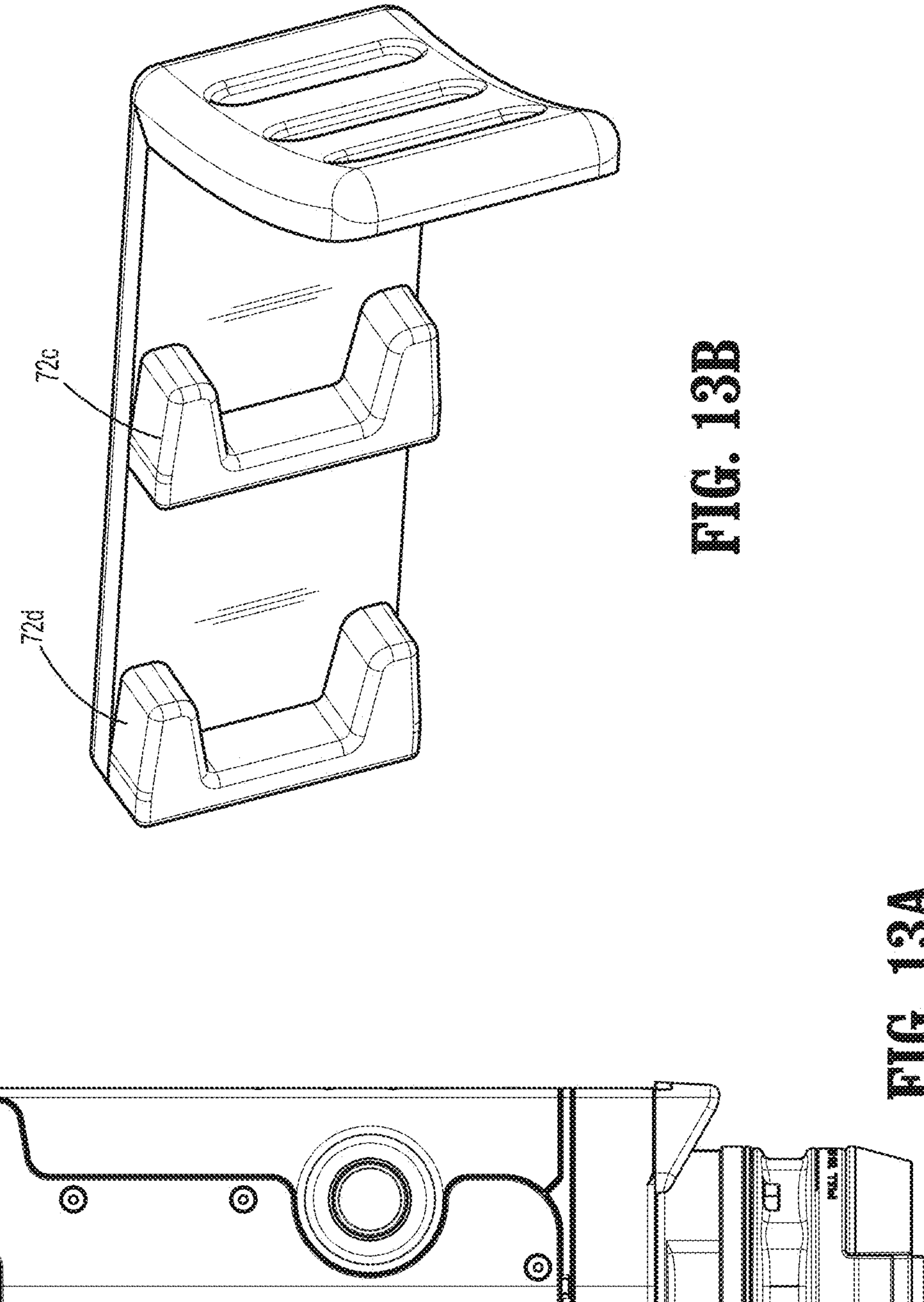
FIG. 13A is a side view of the sterile interface module of FIGS. 4 and 5 coupled to an instrument drive unit of the robotic surgical assembly of FIGS. 2 and 3.
FIG. 13B is an enlarged, perspective view of a button of the instrument drive unit of FIG. 13A.
Figure 13D:
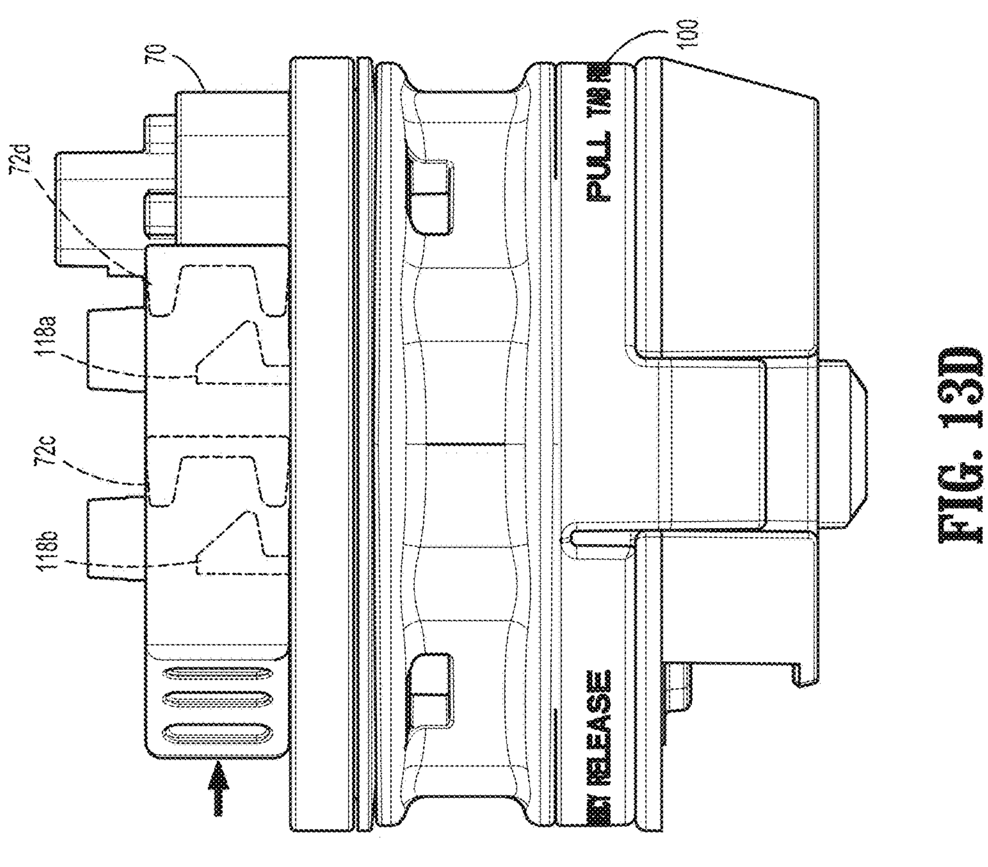
FIG. 13D is a side view of the sterile interface module of FIGS. 4 and 5 and a portion of the instrument drive unit of FIG. 13A with the button of the instrument drive unit shown in a second position.
Figure 13C:
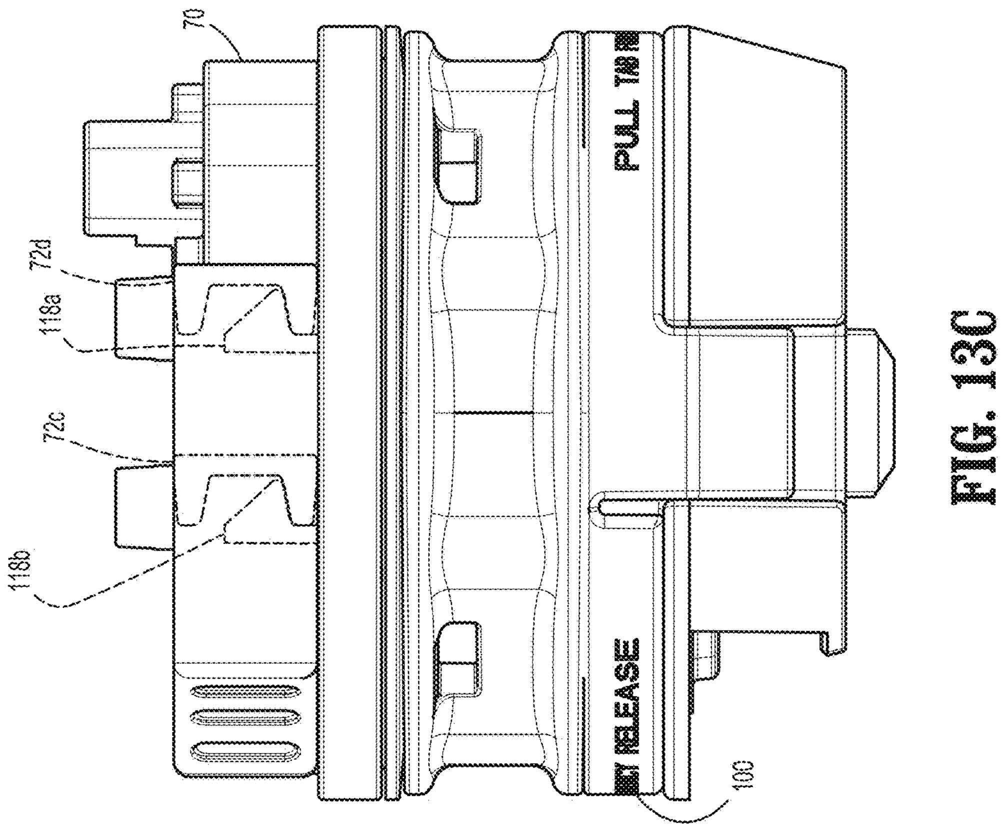
FIG. 13C is a side view of the sterile interface module of FIGS. 4 and 5 and a portion of the instrument drive unit of FIG. 13A with the button of the instrument drive unit shown in a first position.

For example, with the sterile interface module 100 attached to the instrument drive unit 70, depression of the buttons 72*a*, 72*b* slides the protuberances 72*c*, 72*d* of the respective buttons 72*a*, 72*b* relative to the attachment nubs 118*a*-118*d* of the sterile interface module 100, as seen in FIGS. 13C and 13D. Such relative movement separates the attachment nubs 118*a*-118*d* of the sterile interface module 100 from the protuberances 72*c*, 72*d* of the respective buttons 72*a*, 72*b*, whereby the sterile interface module 100 can separate from the instrument drive unit 70 (e.g., by pulling the sterile interface module 100 away from the instrument drive unit 70). Similarly, attachment of the sterile interface module 100 can be effectuated by depressing the buttons 72*a*, 72*b* so that the attachment nubs 118*a*-118*d* of the sterile interface module 100 can be inserted adjacent to the one or more protuberances 72*c*, 72*d* of the buttons 72*a*, 72*b*, whereby release of the depressed buttons 72*a*, 72*b* causes the protuberances 72*c*, 72*d* to bias into engagement with the respective attachment nubs 118*a*-118*d*. Alternatively and/or additionally, the protuberances 72*c*, 72*d* and the attachment nubs 118*a*-118*d* can be configured to cam along one another such that the sterile interface module 100 can be coupled to the instrument drive unit 70 via push-in and/or snap-fit connection.

Referring again to FIGS. 2 and 3, the distal end portion of the instrument drive unit 70 further supports a ring member 80 having a sterile drape 82 secured thereto. The ring member 80 is secured to the distal end of the instrument drive unit 70 via a unilateral axial attachment (e.g., push-in, snap-fit, and/or loose-fit type arrangement), whereby removal of the ring member 80 from the instrument drive unit 70 may be effectuated laterally (e.g., via sliding and/or rotational movement relative to the instrument drive unit 70). In some embodiments, ring member 80 may be supported (e.g., loosely) between the instrument drive unit 70 and the sterile interface module 100, and may be trapped between the instrument drive unit 70 and the sterile interface module 100 until the sterile interface module 100 is uncoupled from instrument drive unit 70. The sterile drape 82 is configured to overlie the robotic surgical assembly 50 and the robotic arms 2, 3 and the sterile drape 82 may be arranged as desired above about the robotic surgical assembly 50 and the robotic arms 2, 3 to provide a sterile barrier between the various aforementioned components and/or the surgical site/fluids and the electromechanical surgical instrument 60. Ring member 80 is configured to be disposed between the instrument drive unit 70 and the sterile interface module 100, and to enable operative interconnection between the instrument drive unit 70 and the sterile interface module 100.

Turning now to FIGS. 4-10, the sterile interface module 100 of the robotic surgical assembly 50 is provided for selectively interconnecting the robotic surgical assembly 50 and the electromechanical surgical instrument 60. The electromechanical surgical instrument 60 may be laterally coupled (e.g., side-loaded) to, or laterally decoupled from, the sterile interface module 100 of the robotic surgical assembly 50. In general, the sterile interface module 100 functions to provide an interface between the instrument drive unit 70 and an electromechanical surgical instrument such as electromechanical surgical instrument 60. This interface advantageously maintains sterility, provides a means to transmit electrical communication between the robotic surgical assembly 50 and the electromechanical surgical instrument 60, provides structure configured to transfer rotational force from the robotic surgical assembly 50 to the electromechanical surgical instrument 60 for performing a function with the electromechanical surgical instrument 60, and/or provides structure to selectively attach/remove the electromechanical surgical instrument 60 to/from the robotic surgical assembly 50 (e.g., for rapid instrument exchange).

Figure 4:
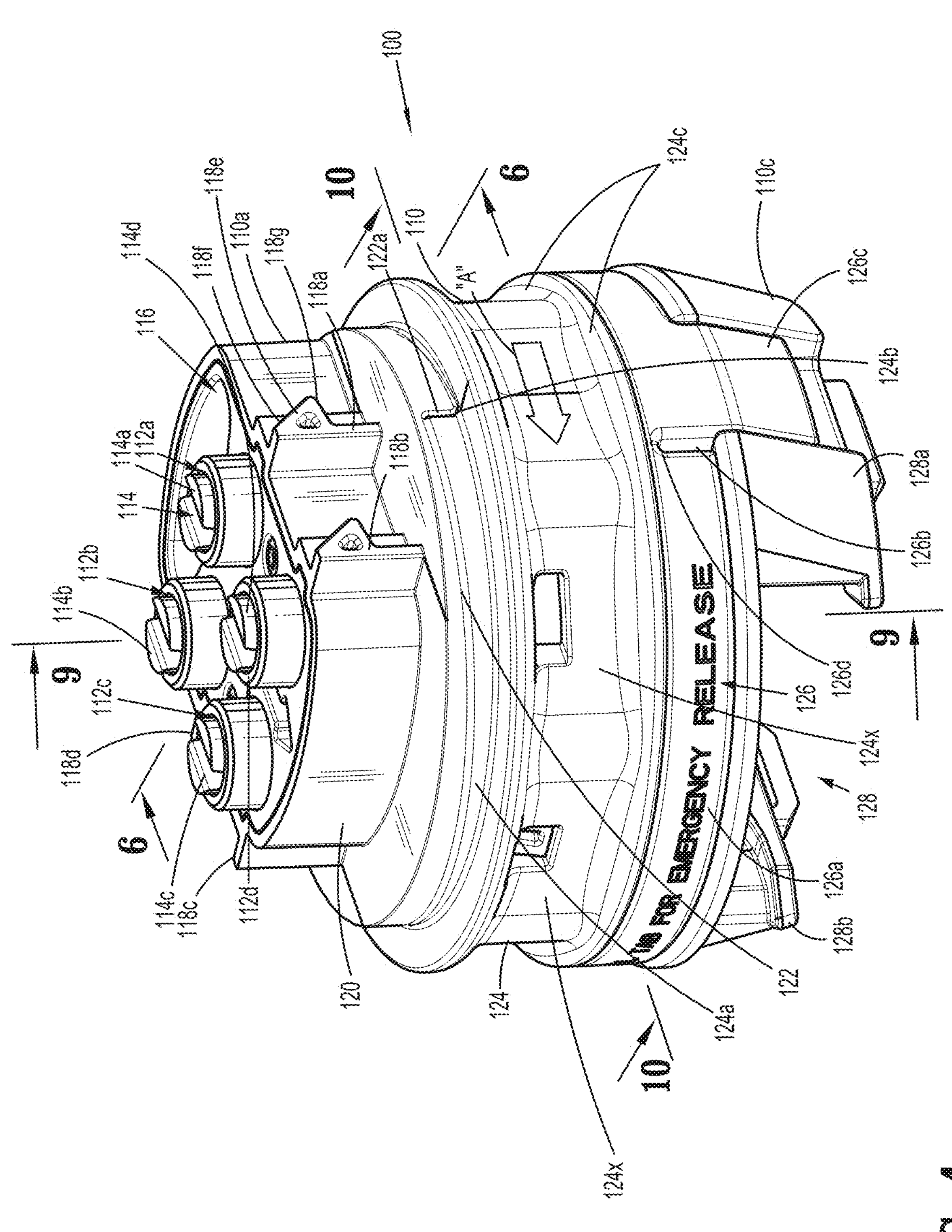
FIG. 4 is front, perspective view of a sterile interface module of the robotic surgical assembly of FIGS. 2 and 3.
Figure 5:
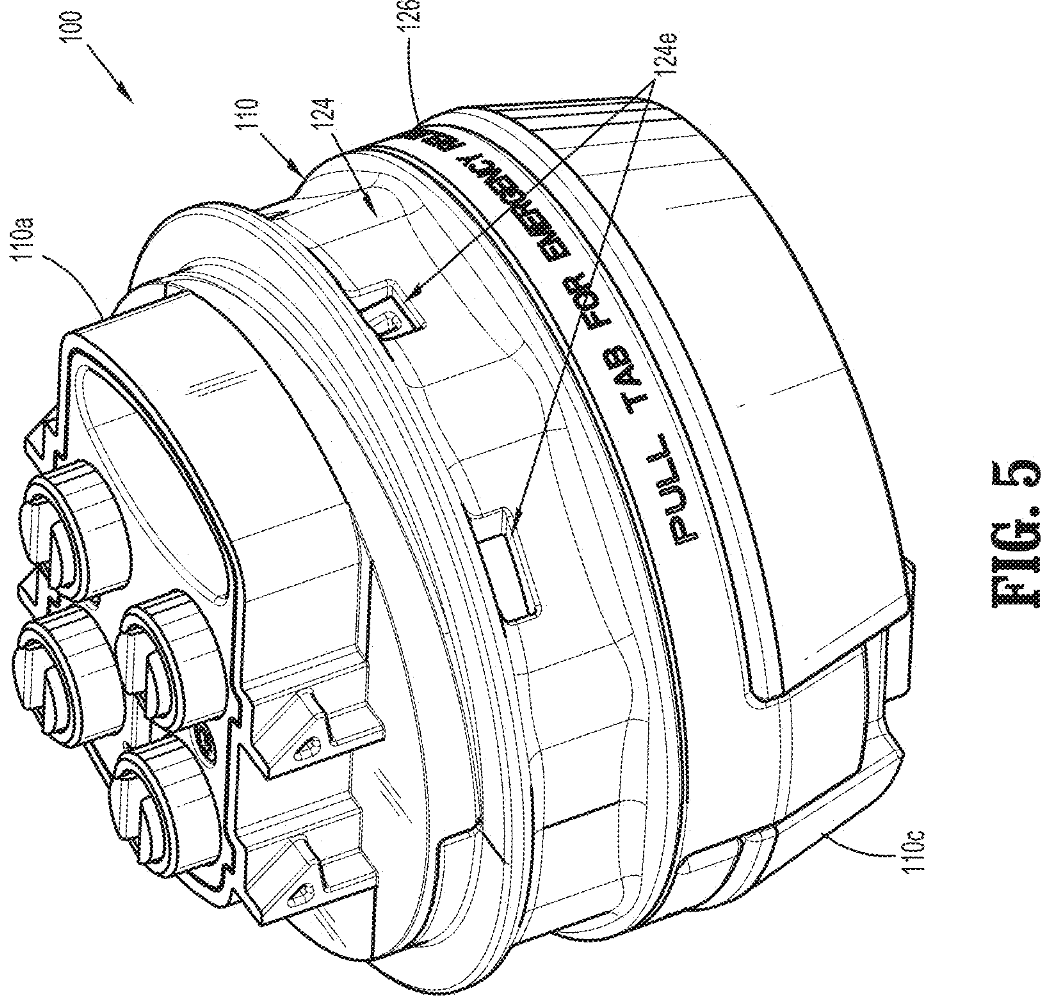
FIG. 5 is a rear, perspective view of the sterile interface module of FIG. 4.
Figure 6:
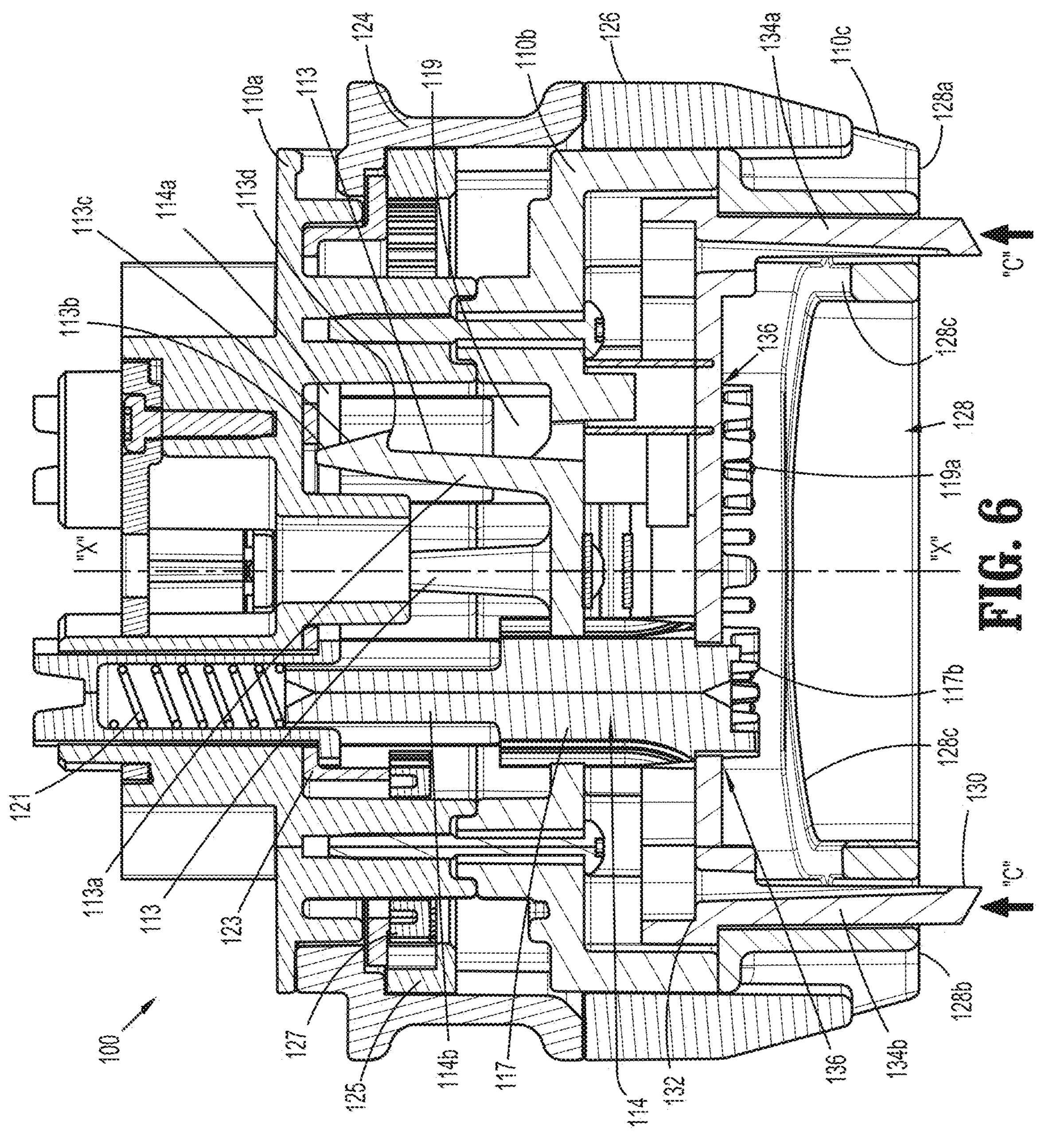
FIGS. 6-8 are progressive, cross-sectional views of the sterile interface module of FIG. 4, as taken along line 6-6 shown in FIG. 4, illustrating a decoupling of the sterile interface module from the robotic surgical assembly of FIGS. 2 and 3.

As seen in FIGS. 4-6, the sterile interface module 100 includes a body member 110 having an upper portion 110*a*, an intermediate portion 110*b* (FIG. 6), and a lower portion 110*c* that are coupled together by one or more fasteners “F” such as screws 101*a*, 101*b*, 101*c*. The sterile interface module 100 includes pins 101*d* (e.g., pogo pins) (FIG. 11) that provide electrically conductive pathways through the sterile interface module 100 (e.g., to an end effector 60*a* of an electromechanical surgical instrument 60 when electromechanical surgical instrument 60 is coupled to the sterile interface module 100—see FIG. 1). The upper portion 110*a* of the body member 110 defines drive transfer channels 112*a*, 112*b*, 112*c*, 112*d* that support drive transfer assemblies 114, such as respective drive transfer assemblies 114*a*, 114*b*, 114*c*, 114*d*, therein. The upper portion 110*a* of the body member 110 further includes a cover 110*z* (FIG. 11) that defines an electrical connector channel or socket 116. The socket 116 enshrouds a first electrical connector 116*a* (FIG. 10) of an electrical assembly 116*x* (FIG. 11) therein. The first electrical connector 116*a* (e.g., pins thereof), which function as an electrical interface, may be recessed within the socket 116 and/or shrouded to protect against damage (e.g., from dropping and/or from mating and/or unmating to the instrument drive unit. The electrical assembly 116*x* is described in greater detail below.

The sterile interface module 100 includes the attachment nubs 118*a*, 118*b*, 118*c*, 118*d*, which extend around or project from opposed sides of a side wall 120 of the upper portion 110*a*. As detailed herein, the attachment nubs 118*a*, 118*b*, 118*c*, 118*d* function to selectively couple the sterile interface module 100 to the robotic surgical assembly 50. The attachment nubs 118*a*, 118*b*, 118*c*, 118*d* may have a flag shape to facilitate engagement with the buttons 72*a*, 72*b* of the instrument drive unit 70. Each of the attachment nubs 118*a*, 118*b*, 118*c*, 118*d* includes a head 118*e* having a tapered cam surface 118*f* and a lip 118*g* that cooperate with the buttons 72*a*, 72*b* (see FIG. 2) of the instrument drive unit 70 to selectively couple the sterile interface module 100 to the instrument drive unit 70.

The upper portion 110*a* of the body member 110 further defines a distally oriented tapered wall or surface 122, which may be helical, and which extends around the upper portion 110*a* from a shoulder 122*a* of the upper portion 110*a*.

With reference to FIG. 6, the intermediate portion 110*b* of the body member 110 includes resilient tabs 113 extending proximally therefrom. The tabs 113, which may include any number of tabs 113, are disposed in spaced-apart relation to one another and may be disposed in circumferential relation about a longitudinal axis “X” defined through the sterile interface module 100 (e.g., four tabs 113 separated by 90 degree intervals). The tabs 113 may be formed of a flexible material and may be configured to flex radially outward. Each of the tabs 113 includes a shaft 113*a* extending proximally to a head 113*b*. The head 113*b* of each respective tab 113 includes an angled cam surface 113*c* that extends to a transverse lip 113*d*.

The intermediate portion 110*b* of the body member 110 movably supports a decoupling collar 124 thereon and removably supports an emergency release ring 126 thereon. The release ring 126 may function to provide fluid and/or dust resistance and/or sealing for the body member 110. In some embodiments, the release ring 126 may provide hermetic sealing.

With reference again to FIG. 4, the decoupling collar 124 defines a tapered ramp 124*a* that extends from a shoulder 124*b* of the decoupling collar 124. The tapered ramp 124*a* of the decoupling collar 124 and the shoulder 124*b* of the decoupling collar 124 complement the tapered wall 122 and the shoulder 122*a* of the upper portion 110*a* of the body member 110.

The decoupling collar 124 further includes scallops or gripping grooves 124*c* about an outer surface thereof to facilitate user gripping and/or movement of the decoupling collar 124 relative to the body member 110 of the sterile interface module 100. For example, as described in greater detail below, the decoupling collar 124 may be rotatable (and/or axially translatable) relative to the body member 110, as indicated by arrow “A”, after the release ring 126 is removed from the body member 110. Each gripping groove 124*c* may include a flat 124*x* (FIG. 4) such that the decoupling collar 124 includes an array of flats 124*x* about the outer surface of the decoupling collar 124 that further facilitate gripping and/or movement of the decoupling collar 124.

The decoupling collar 124 further defines a flange channel 124*d* (FIG. 7) on an inner surface thereof. The decoupling collar 124 may also include any number of vents 124*e* for cooling one or more electrical components of sterile interface module 100 and/or instrument drive unit 70. In particular, rotation or activation of a cooling fan (not shown) of instrument drive unit 70, for example, may draw external air internally into the sterile interface module 100 through the vents 124*e* of sterile interface module 100 so that the air can travel along one or more air flow pathways (see air flow pathways “AA” and “AB” illustrated in FIG. 9) that extend through sterile interface module 100 and/or instrument drive unit 70, thereby cooling electrical components thereof as the air travels therealong. Alternatively, and/or additionally, air internally disposed in sterile interface module 100 and/or instrument drive unit 70 (e.g., hot air generated from operation of the electrical components thereof) can be externally discharged from the vents 124*e*, for instance, as the cooling fan is activated or rotated (e.g., which generates a compression force that causes the air to be externally discharged).

As illustrated in FIG. 4, the release ring 126 of the sterile interface module 100 includes a body portion 126*a* defining one or more separation slots 126*b*, and one or more tabs 126*c* that extend from the body portion 126*a*. Each separation slot 126*b* may be disposed adjacent to frangible segment 126*d* of the body portion 126*a*. The frangible segment 126*d* is configured to break upon a movement of one of the one or more tabs 126*c* relative to the body portion 126*a* of the release ring 126 so that the release ring 126 can be separated from the sterile interface module 100 to enable the decoupling collar 124 to move relative to the body member 110 of the sterile interface module 100.

As illustrated in FIGS. 6-10, the lower portion 110*c* of the body member 110 is in the form of a semi-annular coupling cuff that is supported on or otherwise secured to a distal end of the intermediate portion 110*b* of the body member 110. The lower portion 110*c* of the body member 110 includes a U-shaped body having an instrument opening 128 defined between side arms 128*a*, 128*b* and opening distally and laterally. The lower portion 110*c* further includes a ramped surface 128*c* formed on an inner surface thereof that complements ramped camming surfaces 61*a*, 61*b* (FIG. 2) disposed on an outer surface of the instrument housing 61 of the electromechanical surgical instrument 60. The instrument opening 128 is configured to receive an electromechanical surgical instrument, such as electromechanical surgical instrument 60, therein to removably secure the electromechanical surgical instrument 60 to the robotic surgical assembly 50. The side arms 128*a*, 128*b* of the lower portion 110*c* extend distally from the intermediate portion 110*b* of the body member 110 and are positioned to support the electromechanical surgical instrument 60 within the instrument opening 128 of the lower portion 110*c*.

As seen in FIG. 6, the sterile interface module 100 further includes a floating plate 130 supported between the intermediate portion 110*b* of the body member 110 and the lower portion 110*c* of the body member 110. The floating plate 130 of the sterile interface module 100 is movable between an uncompressed position or extended position and a compressed or retracted position. The floating plate 130 is spring biased distally toward the uncompressed position biasing members of the drive transfer assemblies 114*a*, 114*b*, 114*c*, 114*d* (FIG. 4) of the sterile interface module 100. In some embodiments, by a round spring (e.g., a wave spring) or the like (not shown) may be used to distally bias the floating plate 130 to the uncompressed position. The floating plate 130 includes a base portion 132 and tabs 134*a*, 134*b* extending distally from the base portion 132. The tabs 134*a*, 134*b* of the floating plate 130 extend through the lower portion 110*c* of the body member 110. The floating plate 130 defines apertures 136 therein that receive the drive transfer assemblies 114*a*, 114*b*, 114*c*, 114*d* of the sterile interface module 100. The floating plate 130 may function to prevent perpendicular loads acting on the drive transfer assemblies 114*a*, 114*b*, 114*c*, 114*d*, for example, upon a side loading of an electrosurgical instrument to the sterile interface module 100.

Figure 7:
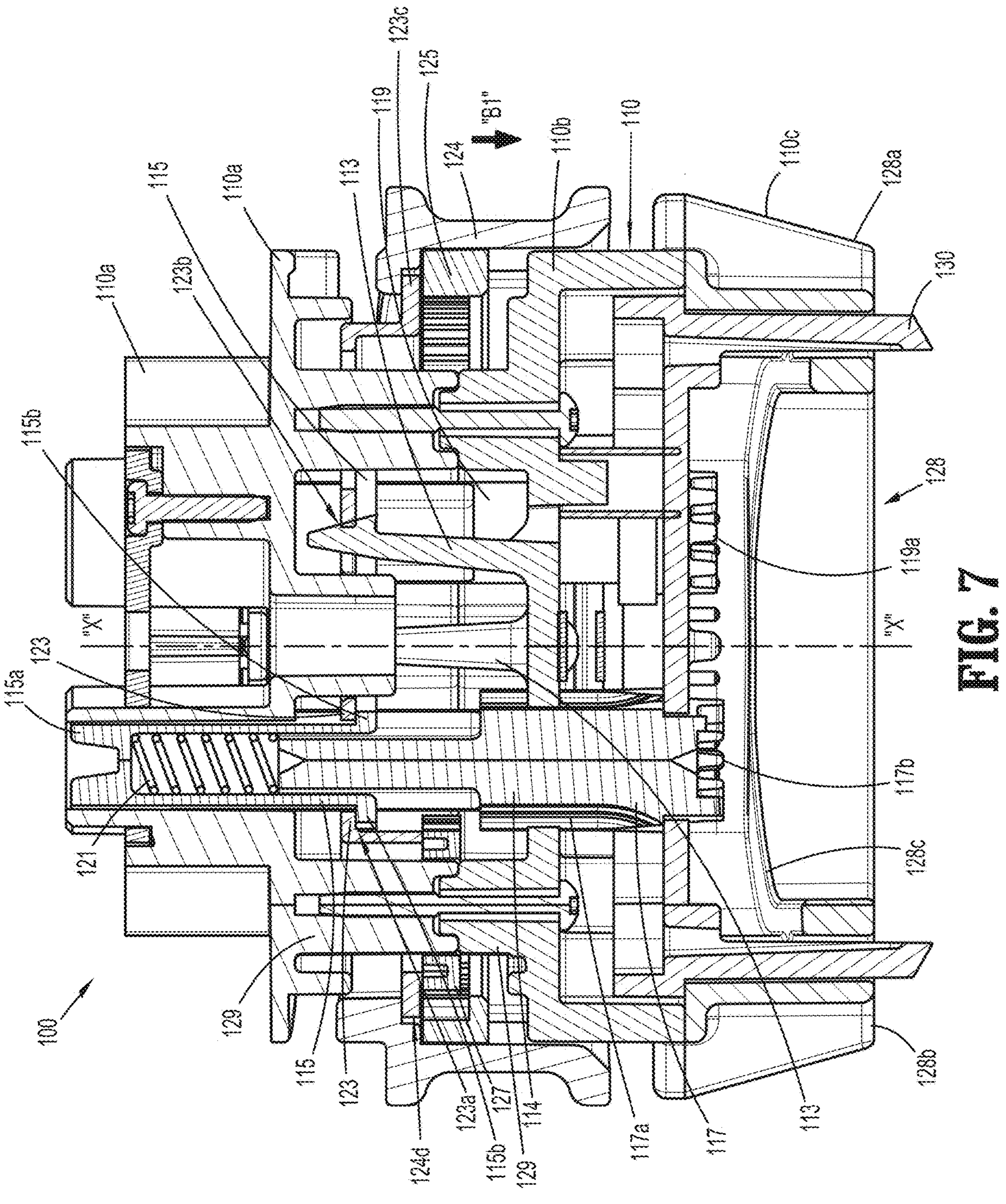

As seen in FIGS. 6 and 7, the sterile interface module 100 further includes a support plate 123 coupled to the decoupling collar 124. The support plate 123 defines coupling openings 123*a* in registration with the drive assemblies 114 of the sterile interface module 100, and tab apertures 123*b* in registration with the tabs 113 of the intermediate portion 110*b* of the sterile interface module 100. The tab apertures 123*b* may be configured to impart a radial inward flex on the tabs 113 (e.g., the shafts 113*a* of the tabs 113) as the angled cam surfaces 113*c* of the heads 113*b* of the tabs 113 cam along the tab apertures 123*b* of the support plate 123, as detailed below. The support plate 123 includes a flange 123*c* that is received within the flange channel 124*d* of the decoupling collar 124 to enable the support plate 123 to move with the decoupling collar 124.

Figure 8:
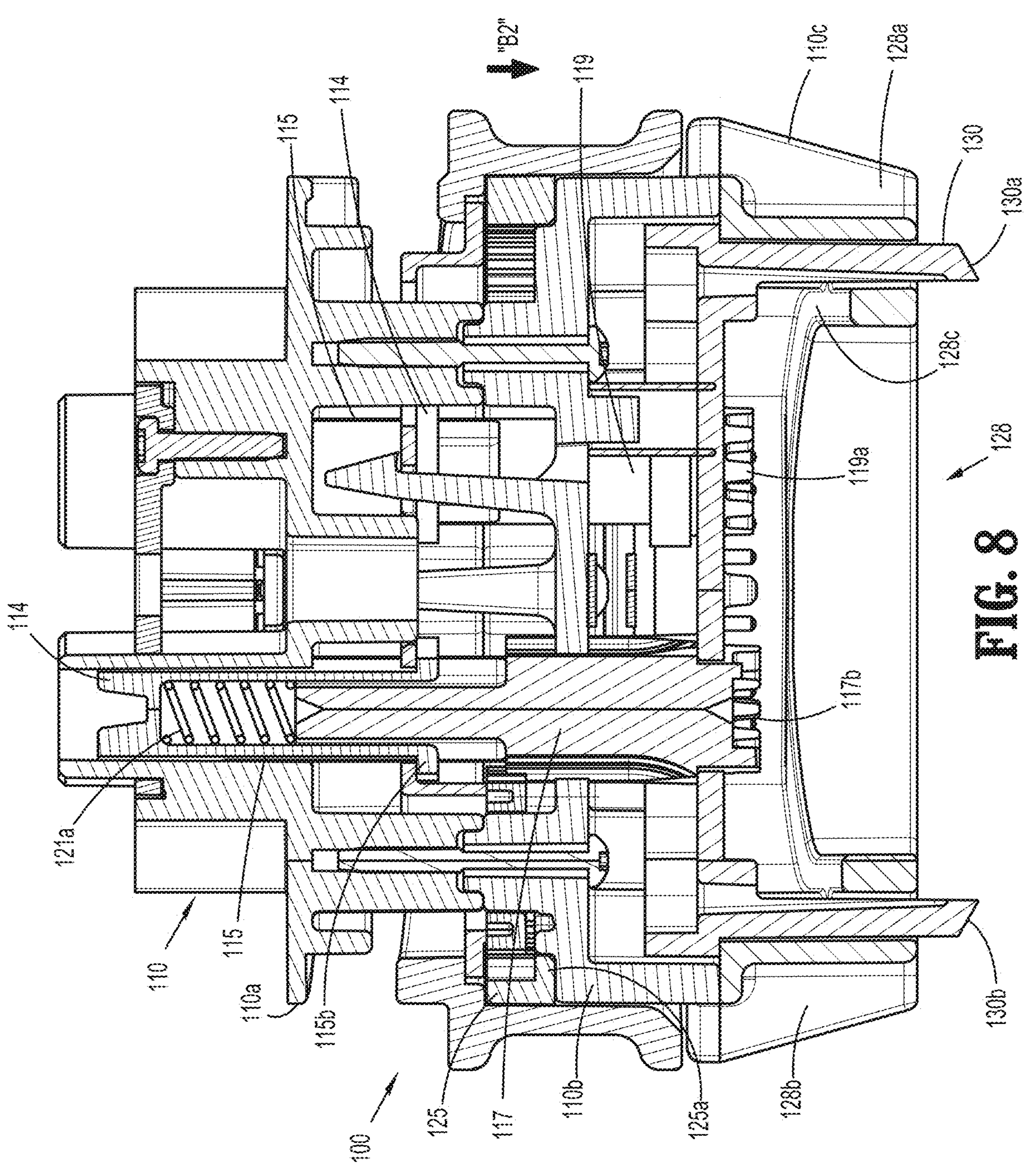

The sterile interface module 100 further includes a ring coupler 125 coupled to the decoupling collar 124 and in contact with a bottom surface of the flange 123*c* of the support plate 123 so that the decoupling collar 124 can rotate around the flange 123*c* of the support plate 123, as indicated by arrow "A" (FIG. 4), while axially moving the support plate 123 as the rotation of the decoupling collar 124 axially translates the decoupling collar 124 relative to the longitudinal axis "X," as indicated by arrow "B1." The decoupling collar 124 may be axially moveable relative to the body member 110 without rotation, as indicated by arrow "B2" (FIG. 8).

Figure 9:
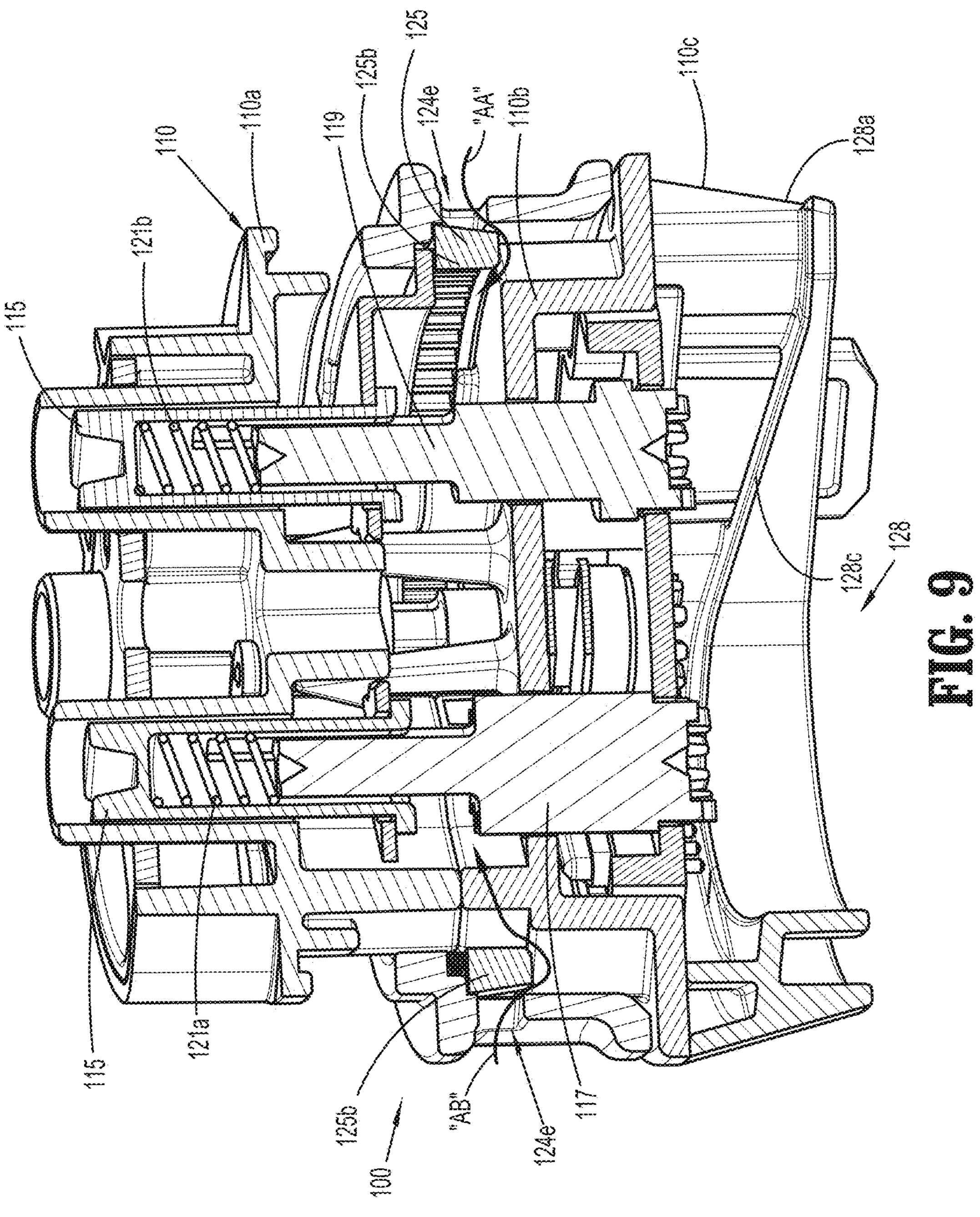
FIG. 9 is a cross-sectional view of the sterile interface module of FIG. 4, as taken along line 9-9 shown in FIG. 4.

As seen in FIG. 8, the ring coupler 125 includes a ledge 125*a* that extends radially inward from the ring coupler 125 along at least a portion of a circumference of the ring coupler 125 to support idler coupler 127. With reference also to FIG. 9, the ring coupler 125 further includes a transverse cross-section having a tapered profile 125*b* along at least portions of the ring coupler 125. For example, the ring coupler 125 may include a tapered profile 125*b* adjacent to one or more of the vents 124*e* of the decoupling collar 124. The tapered profile 125*b* may be positioned in fluid communication with one or more of the vents 124*e* to provide one or more air flow pathways, such as air flow pathways "AA" and "AB" illustrated in FIG. 9, between the ring coupler 125 and the decoupling collar 124.

The air flow pathways "AA" and "AB" function to aid in maintaining component sterility and cooling various components (e.g., motors, sensors, etc.) of the robotic surgical system 1 (e.g., the sterile interface module 100, instrument drive unit 70, etc.) The air flow pathways provide a balanced cross-sectional area of air flow from outside the sterile interface module and into the instrument drive unit for cooling and thermal management. The air flow pathways provide a tortuous path for air flow through the sterile interface module and into the instrument drive unit. Vents may be shaped to a desired symbology such as loading or unloading direction use of arrows. Symbology may be molded in and/or laser etched and positioned for instructional indicia pertaining to use, loading, removal, mating and/or warnings.

With reference to FIG. 7, the sterile interface module 100 also includes an idler coupler 127 that is coupled to the ring coupler 125 and supported on the ledge 125*a* of the ring coupler 125. The idler coupler 127 is rotatably supported on a coupling shaft 129 that interconnects the upper and intermediate portions 110*a*, 110*b* of the body member 110. The idler coupler 127 is axially slidable along the coupling shaft 129 as the decoupling collar 124 rotates about the longitudinal axis "X" and/or axially moves relative to the body member 110, as detailed herein.

With reference to FIGS. 3 and 7, each of the drive transfer assemblies 114 of the sterile interface module 100 includes a drive coupler 115 defining a coupling end 115*a* (e.g., a slot) engagable with one of the respective motor couplers 76 of the motor assembly 74 on a proximal end of the drive coupler 115. Drive coupler 115 further includes a flange

115*b* on a distal end thereof. Each drive coupler 115 extends through one of the coupling openings 123*a* of the support plate 123 of the sterile interface module 100. The support plate 123 is coupled to the decoupling collar 124 so that a bottom surface of the support plate 123 is in contact with a top surface of the flange 115*b* of the drive couplers 115 of the drive transfer assemblies 114. Each of the drive transfer assemblies 114 includes a first transfer shaft 117 or a second transfer shaft 119. The first transfer shaft 117 includes a radial coupler 117*a* extending radially outward from the transfer shaft 117, and a distal coupler 117*b* extending distally from the transfer shaft 117. The second transfer shaft 119 includes a distal coupler 119*a* that extends distally from the transfer shaft 119. The distal couplers 117*b* and 119*a* of the respective first and second transfer shafts 117, 119 are configured to engage corresponding couplers (not shown) of the driven members 62*a*, 62*b*, 62*c*, etc. of the electromechanical surgical instrument 60. Any of the couplers described herein may be in the form of a gear having any number of teeth.

Each of the drive transfer assemblies 114 of the sterile interface module 100 includes a spring 121 to enable components of the respective drive transfer assemblies 114 to move relative to one another. As seen in FIGS. 8 and 9, for example, a first spring 121*a* is supported between the first transfer shaft 117 and its respective drive coupler 115, and a second spring 121*b* is supported between the second transfer shaft 119 and its respective drive coupler 115. Each spring 121 is configured to apply spring force to its respective drive transfer assembly 114 upon compression thereof.

Figure 10:
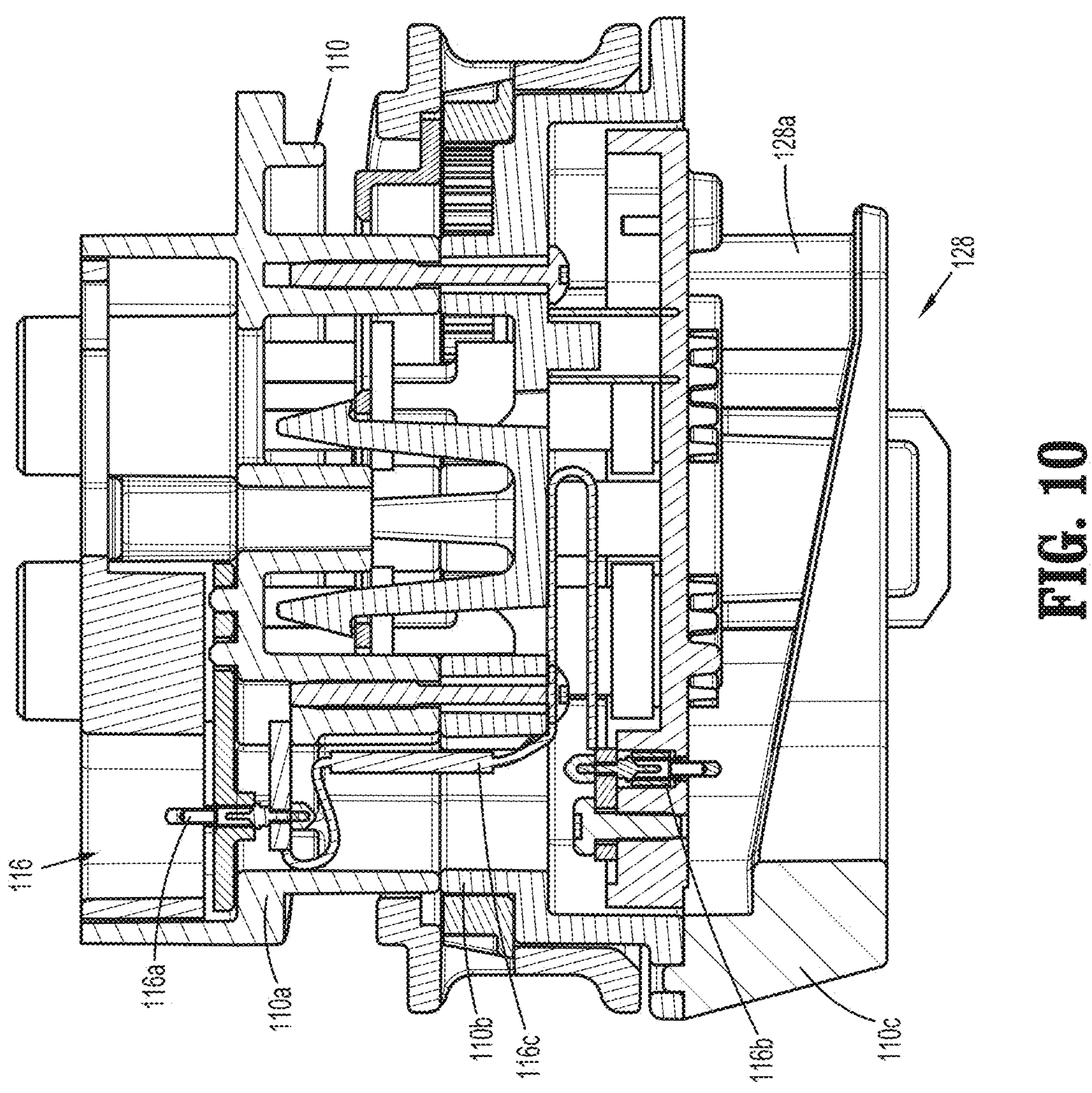
FIG. 10 is a cross-sectional view of the sterile interface module of FIG. 4, as taken along line 10-10 shown in FIG. 4.
Figure 11:
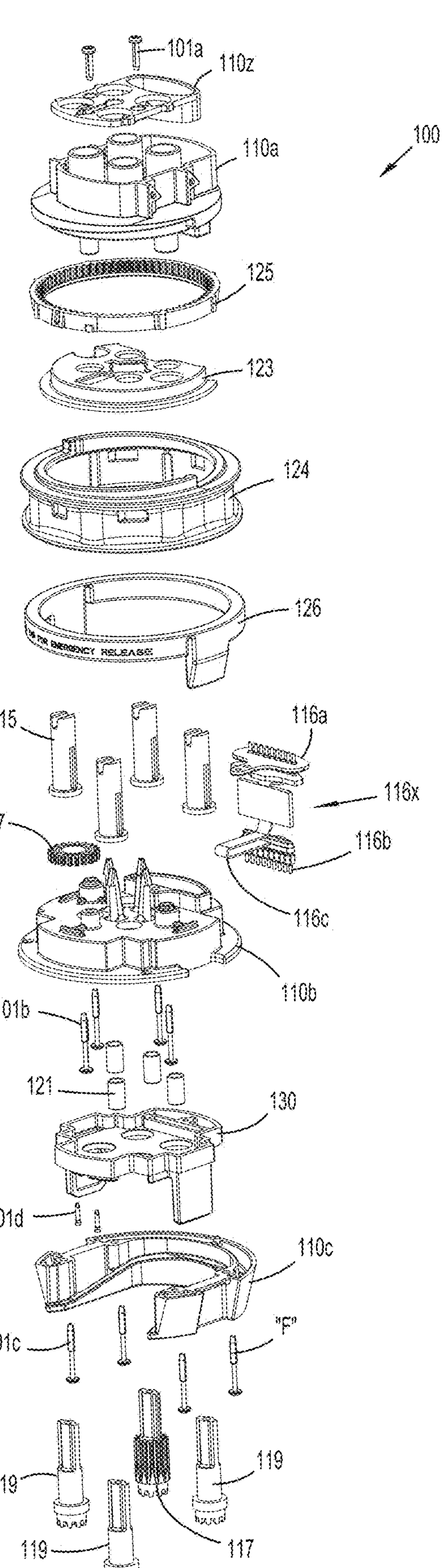
FIG. 11 is front, perspective view, with parts separated, of the sterile interface module of FIGS. 4 and 5.

As seen in FIGS. 10 and 11, the sterile interface module 100 includes an electrical assembly 116*x* including the first electrical connector 116*a*, a second electrical connector 116*b*, and an electrical ribbon 116*c* coupled between the first and second electrical connectors 116*a*, 116*b* to provide electrical communication between the robotic surgical assembly 50 and any electromechanical surgical instrument, such as electromechanical surgical instrument 60, coupled thereto. The electrical assembly 116*x* may include a counter (not shown) configured to measure use of the sterile interface module 100, for example, to account for degradation of spring pins 116*d* of one or both of the electrical connectors 116*a*, 116*b* over time such that the sterile interface module 100 can be replaced as necessary or desired.

With reference to FIGS. 2, 6 and 14A-14C, to couple an electromechanical surgical instrument, such as electromechanical surgical instruments 60, to the sterile interface module 100, the ramped camming surfaces 61*a*, 61*b* of the electrosurgical surgical instrument 60 are aligned with the ramped surface 128*c* of the lower portion 110*c* of the sterile interface module 100. The electromechanical surgical instrument 60 is then transversely moved (e.g., side loaded) relative to the robotic surgical assembly 50 until the ramped camming surfaces 61*a*, 61*b* of the electromechanical surgical instrument 60 are fully received or seated on the ramp surface 128*c* of the lower portion 110*c* of the sterile interface module 100.

Figure 14A:
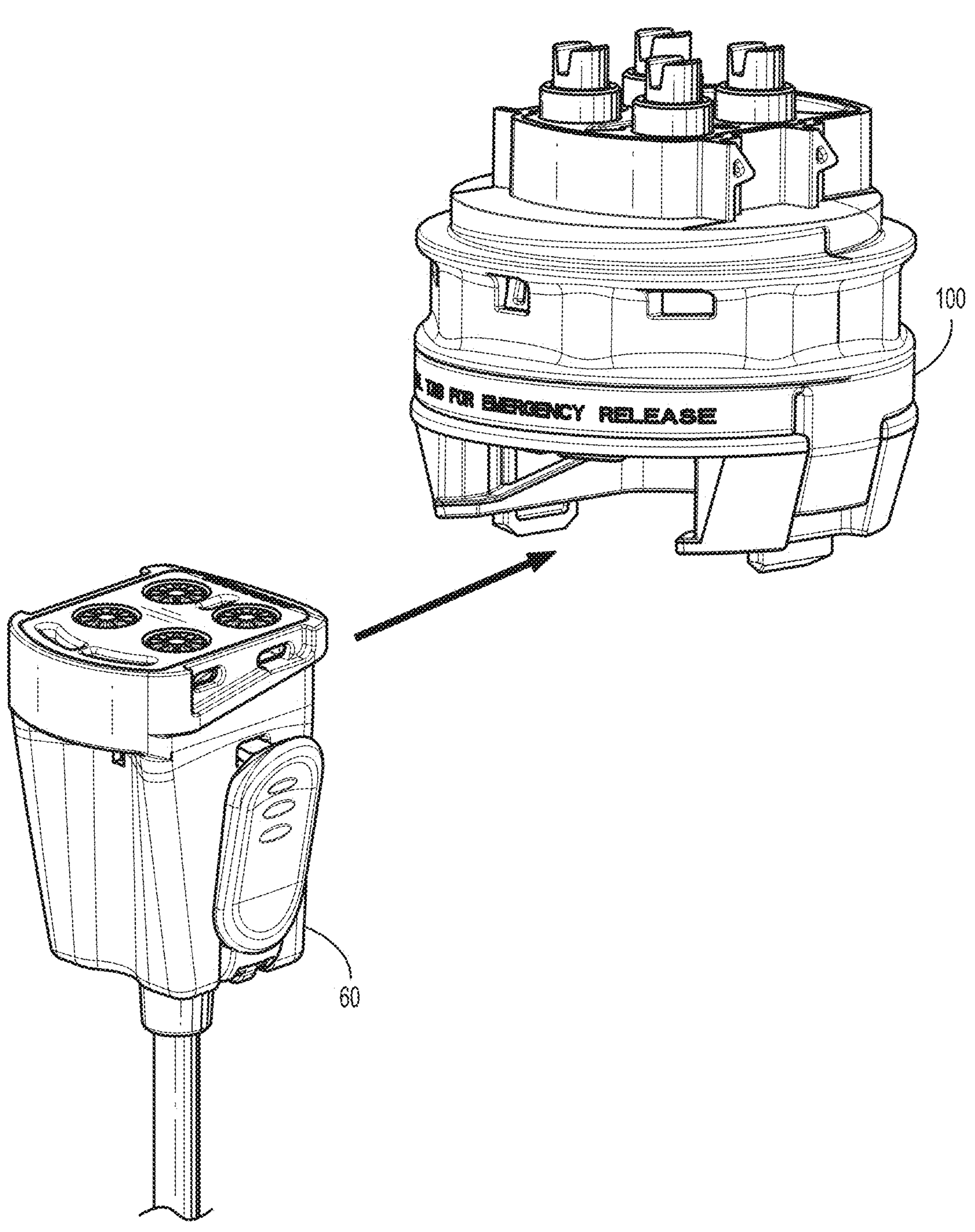
FIGS. 14A-14C are progressive views illustrating the sterile interface module of FIGS. 4 and 5 receiving an electromechanical surgical instrument of the robotic surgical assembly of FIGS. 2 and 3.
Figure 14B:
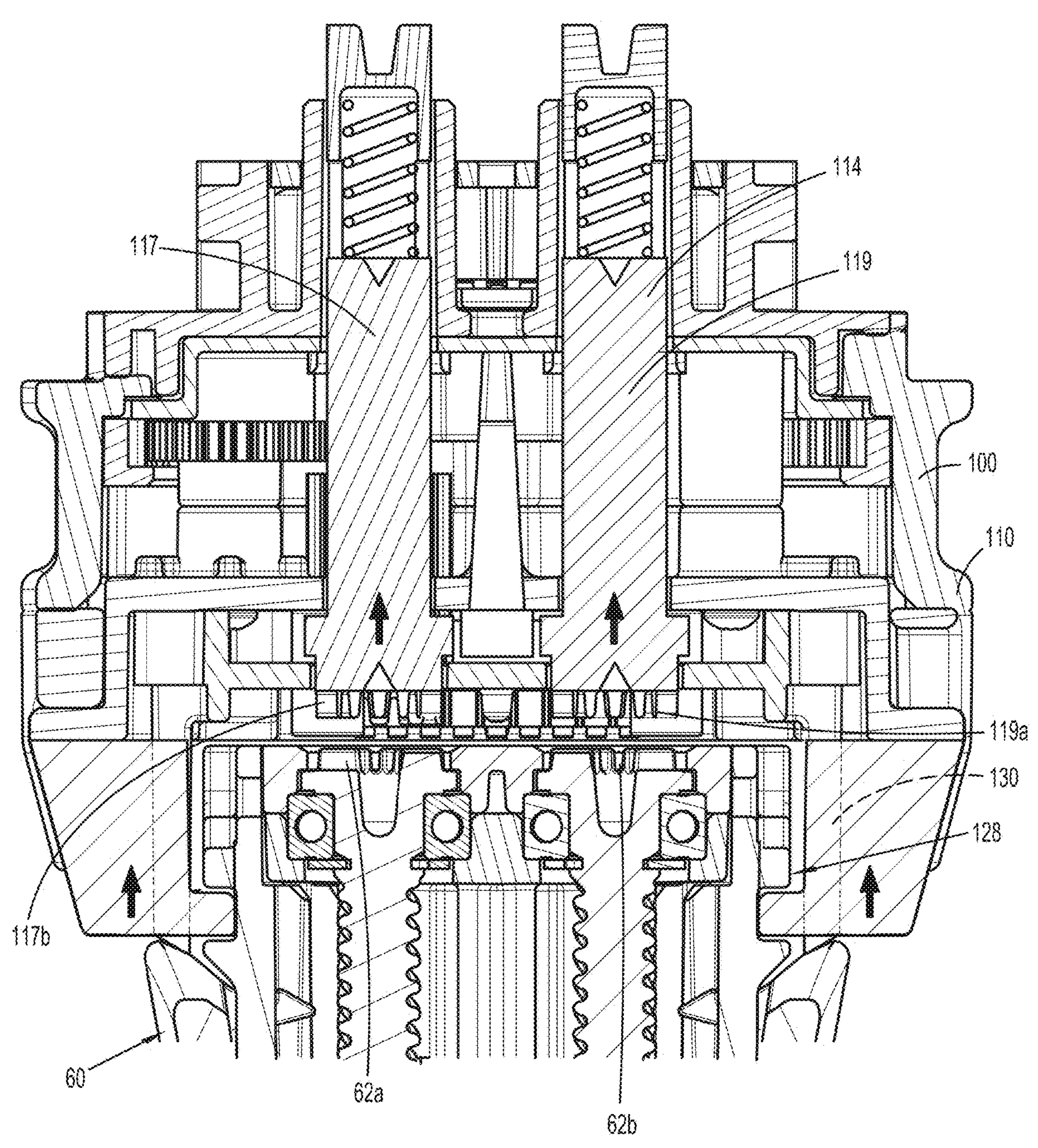
Figure 14C:
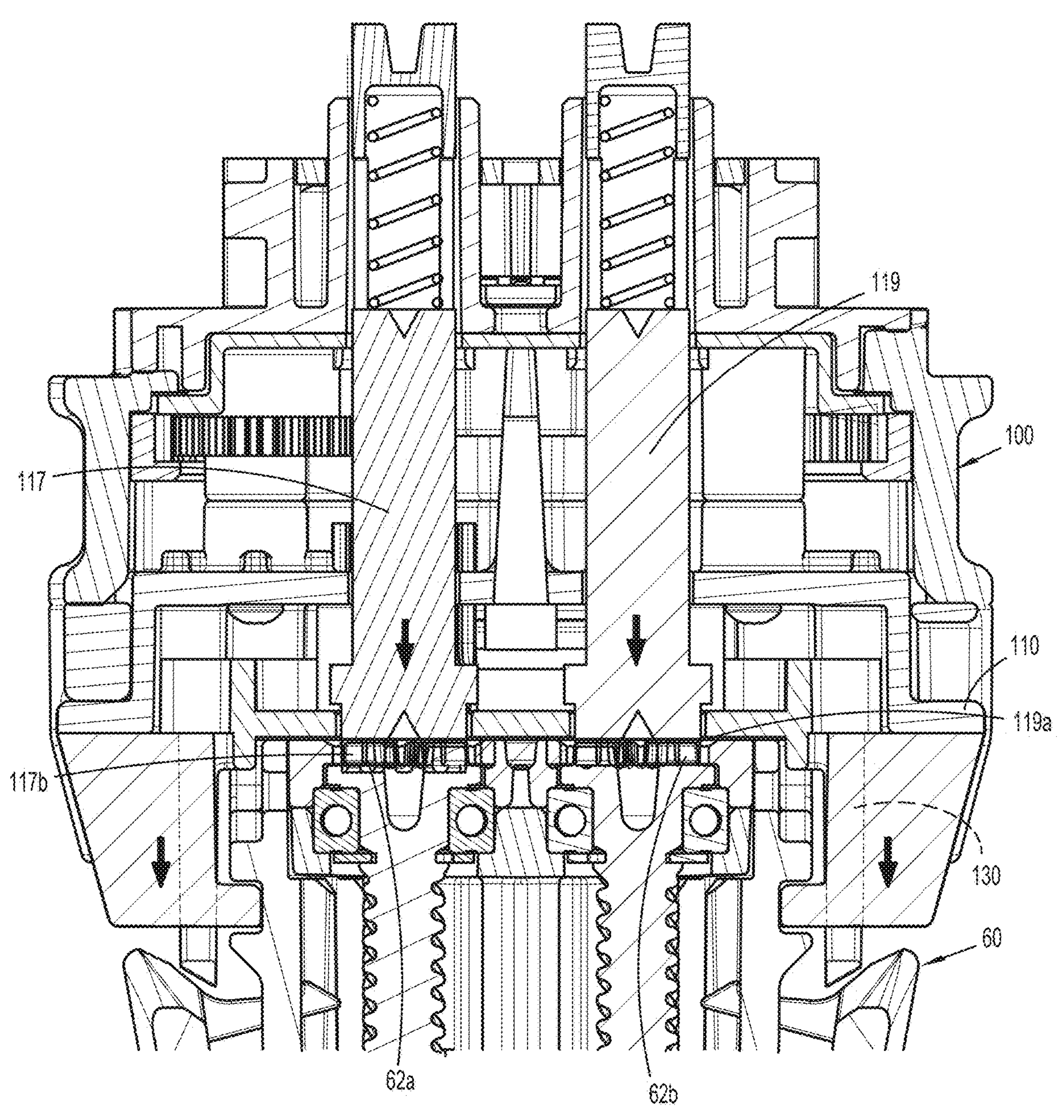

As the electromechanical surgical instrument 60 is transversely moved into the lower portion 110*c* of the sterile interface module 100, the electromechanical surgical instrument 60 cams upwardly to proximally move or compress the floating plate 130 of the sterile interface module 100 relative to the body member 110, as indicated by arrows "C" shown in FIG. 6 (see also FIG. 14B. Movement of the floating plate 130 from its initial extended position (FIG. 14A) into a compressed position (FIG. 14B) draws the transfer shafts 117, 119 (and their corresponding instrument engagement ends 117*b*, 119*a*) of the sterile interface module 100 proximally away from the instrument opening 128 of the lower portion 110*c* of the sterile interface module 100 to facilitate insertion of the electromechanical surgical instrument 60 into the instrument opening 128 of the sterile interface module 100. Moving the floating plate 130 from the extended position (FIG. 14A) to the compressed position (FIG. 14B) helps prevent insertion contact/interference between the distal couplers 117*b*, 119*a* of the drive transfer assemblies 114 of the sterile interface module 100 and corresponding driven members 62*a*, 62*b*, 62*c*, etc. of the electromechanical surgical instrument 60 (see FIG. 2).

Once the electromechanical surgical instrument 60 is fully seated within the lower portion 110*c* of the sterile interface module 100, the floating plate 130 of the sterile interface module 100 is urged back to the extended position (FIG. 14C) so that the distal couplers 117*b*, 119*a* of the drive transfer assemblies 114 of the sterile interface module 100 and the corresponding driven members 62*a*, 62*b*, 62*c*, etc. of the electromechanical surgical instrument 60 come into registration with one another to couple the electromechanical surgical instrument 60 to the robotic surgical assembly 50 via the sterile interface module 100.

With the robotic surgical assembly 50 of the robotic surgical system 1 secured to one of the surgical robotic arms 2, 3, of the robotic surgical system 1, and the electromechanical surgical instrument 60 of the robotic surgical system 1 secured to the sterile interface module 100 of the robotic surgical system 1, a clinician can perform a surgical procedure by robotically controlling the driven members 62*a*, 62*b*, 62*c*, etc. of the electromechanical surgical instrument 60 with the motor assembly 74 of robotic surgical assembly 50 as desired. In particular, one or more of the motors 74*a*, 74*b*, 74*c*, etc. of the motor assembly 74 are actuated to rotate one or more of the motor couplers 76*a*, 76*b*, 76*c*, etc. of the of the motor assembly 74 so that one or more of the drive transfer assemblies 114 of the sterile interface module 100 cooperate with one or more of the driven members 62*a*, 62*b*, 62*c*, etc. of the electromechanical surgical instrument 60 to operate and/or manipulate the end effector 60*a* of the electromechanical surgical instrument 60 as desired (e.g., fire, articulate, rotate, etc.).

To remove the electromechanical surgical instrument 60 from the robotic surgical assembly 50, for example, to perform an instrument exchange, a clinician can depress paddles 64*a*, 64*b* of the electromechanical surgical instrument 60 (FIG. 2). Depression of the paddles 64*a*, 64*b* imparts a force on tabs 130*a*, 130*b* (FIG. 8) of the floating plate 130 of the sterile interface module 100 to move the floating plate 130 in a proximal direction relative to the body member 110 of the sterile interface module 100. As the floating plate 130 moves in a proximal direction, the first and second transfer shafts 117, 119 of the respective drive transfer assemblies 114 translate with the floating plate 130 of the sterile interface module 100 in the proximal direction against biasing forces from the springs 121 of the respective drive transfer assemblies 114. Movement of the transfer shafts 117, 119 of the respective drive transfer assemblies 114 relative to the body member 110 of the sterile interface module 100 separates the distal couplers 117*b*, 119*a* of the first and second transfer shafts 117, 119 of the drive transfer assemblies 114 from the respective driven members 62*a*, 62*b*, 62*c*, etc. of the electromechanical surgical instrument 60.

Once the distal couplers 117*b*, 119*a* of the first and second transfer shafts 117, 119 of the respective drive transfer assemblies 114 are separated from the respective driven members 62*a*, 62*b*, 62*c*, etc. of the electromechanical surgical instrument 60, the proximal end of the instrument housing 61 of the electromechanical surgical instrument 60 can be slid laterally out from the instrument opening 128 of the lower portion 110*c* of the body member 110 of the sterile interface module 100.

The electromechanical surgical instrument 60 can be re-attached to the sterile interface module 100 through the instrument opening 128 of the lower portion 110*c* of the body member 110 of the sterile interface module 100 as described above. Alternatively, a different electromechanical surgical instrument (e.g., a stapler, endoscope, forceps, etc.) can be likewise attached as desired.

Figure 12A:
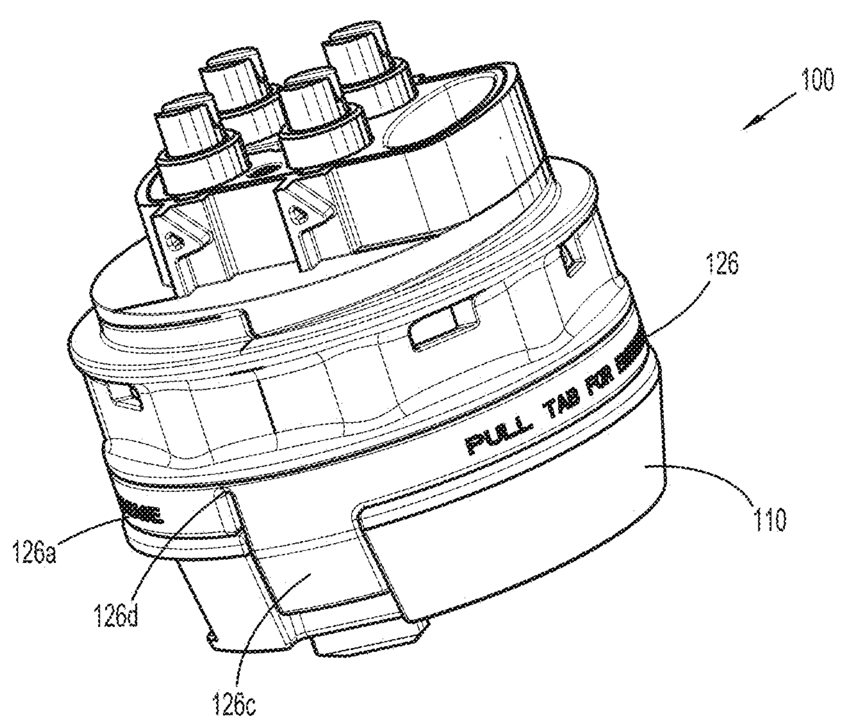
FIGS. 12A and 12B are progressive views of the sterile interface module of FIGS. 4 and 5 illustrating a release ring of the sterile interface module being removed from the sterile interface module.
Figure 12B:
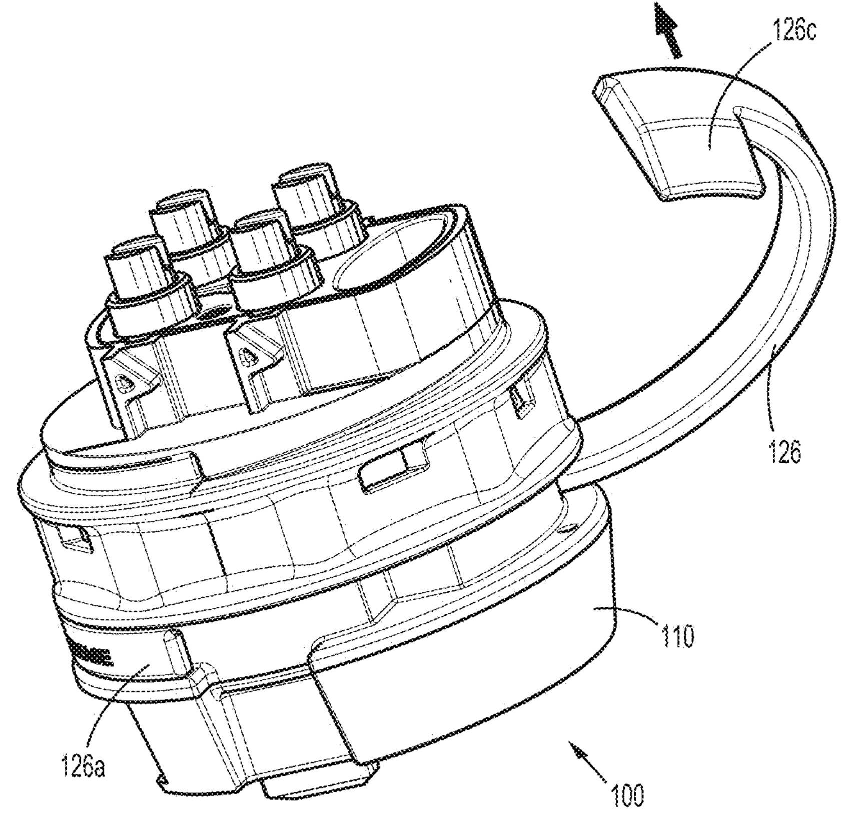

With reference to FIGS. 1, 12A, and 12B, in an emergency situation such as when there is an electrical power failure, and when the electromechanical surgical instrument 60 is at least partially positioned within a patient, the release ring 126 of the sterile interface module 100 can be removed from the body member 110 of the sterile interface module 100. With respect to FIGS. 12A and 12B, the tabs 126*c* of the release ring 126 can be manually manipulated relative to the body portion 126*a* of the release ring 126 until the frangible segment 126*d* of the release ring 126 breaks so that the release ring 126 can be separated from the sterile interface module 100.

With reference to FIGS. 1-11, once the release ring 126 is separated from the sterile interface module 100, the decoupling collar 124 of the sterile interface module 100 can be rotated about the body member 110 of the sterile interface module 100, as indicated by arrow "A," to move the decoupling collar 124 axially in the distal direction from an initial, proximal-most position toward the lower portion 110*c* of the body member 110 of the sterile interface module 100. In effect, such movement of the decoupling collar 124 enables the sterile interface module 100 to provide a manual override function. In the initial, proximal-most position of the decoupling collar 124 (FIG. 6), the ring and idler couplers 125, 127 of the sterile interface module 100 are longitudinally spaced from the radial coupler 117*a* of the first transfer shaft 117 of the sterile interface module 100.

The decoupling collar 124 of the sterile interface module 100 can be moved (e.g., rotationally and/or axially) from the initial, proximal-most position (FIG. 6) to a distal-most position (FIG. 8) through any number of intermediate positions between the proximal-most and distal-most positions. Rotation of the decoupling collar 124 of the sterile interface module 100 (from the proximal-most toward the distal-most position), rotates the ring coupler 125 of the sterile interface module 100, which causes the idler coupler 127 of the sterile interface module 100 to freely rotate about, and/or distally slide along the coupling shaft 129 of the sterile interface module 100.

Continued distal advancement of the idler coupler 127 of the sterile interface module 100, in response to the continued distal movement (e.g., rotational and/or axial movement) of the decoupling collar 124 of the sterile interface module 100 relative to the body member 110 thereof, causes the idler coupler 127 to engage with the radial coupler 117*a* of the first transfer shaft 117 of one of the drive assemblies 114 of the sterile interface module 100. As the decoupling collar 124 advances distally, the decoupling collar 124 draws the support plate 123 of the sterile interface module 100 distally relative to the tabs 113 of the sterile interface module 100 so that the heads 113*b* of the tabs 113 slide through the tab apertures 123*b* of the support plate 123. The angled cam surface 113*c* of the heads 113*b* of the tabs 113 cam along the tab apertures 123*b* as the support plate 123 moves relative to the tabs 113. Distal advancement of the support plate 123 also draws the drive couplers 115 of the drive assemblies 114 distally by virtue of contact between the bottom surface of the support plate 123 and the top surface of the flanges 115*b* of the drive couplers 115 (FIGS. 7 and 8). Distal movement of the drive couplers 115 separates the coupling ends 115*a* of the drive couplers 115 from the respective motor couplers 76 of the motor assembly 74 of the robotic surgical assembly 50 and retracts the drive couplers 115 of the sterile interface module 100 within the drive transfer channels 112*a*, 112*b*, 112*c*, 112*d* of the body member 110 of the sterile interface module 100.

Once the support plate 123 of the sterile interface module 100 is moved distally past the angled cam surfaces 113*c* of the tabs 113 of the sterile interface module 100, the tabs 113 flex outwardly (in response to inward flexing resulting from contact between the heads 113*b* of the tabs 113 and the tab apertures 123*a* of the support plate 123) so that transverse lips 113*d* of the tabs 113 extend over a top surface of the support plate 123 and prevent the support plate 123 from moving proximally (see FIG. 8). In this distal-most position of the support plate 123 and the decoupling collar 124 of the sterile interface module 100, the decoupling collar 124 and the drive couplers 115 of the drive assemblies 114 are also prevented from moving proximally such that the drive couplers 115 cannot reengage with the motor couplers 76 of the motor assembly 74, preventing robotic control of the drive couplers 115.

The distal movement of the decoupling collar 124 of the sterile interface module 100 toward this distal-most position may electrically disconnect one or more of electrical connectors 116*a*, 116*b* and/or the electrical ribbon 116*c* of the sterile interface module 100 so that there is no electrical communication between the robotic surgical assembly 50 and the electromechanical surgical instrument 60. For example, the electrical ribbon 116*c* may be secured to the support plate 123 such that the distal advancement of the decoupling collar 124 relative to the body member 110 of the sterile interface module 100 separates the electrical ribbon 116*c* from the electrical connector 116*a*.

Once the decoupling collar 124 of the sterile interface module 100 is disposed in the distal-most position, rotation of the decoupling collar 124 causes the ring coupler 125 to rotate the idler coupler 127 of the sterile interface module 100. With the idler coupler 127 engaged with the radial coupler 117*a* of the first transfer shaft 117 of the sterile interface module 100, rotation of the idler coupler 127 rotates the radial coupler 117*a* and thereby rotates the distal coupler 117*b* of the first transfer shaft 117. This rotation of the transfer shaft 117 may be independent of the second transfer shafts 119 of the sterile interface module 100 (which may generally remain stationary without robotic control thereof). As the distal coupler 117*b* of the first transfer shaft 117 rotates in response to rotation of the idler coupler 127, the distal coupler 117*b* of the first transfer shaft 117 cooperates with a respective one of the driven members 62*a*, 62*b*, 62*c*, etc. of the electromechanical surgical instrument 60 to advantageously manually manipulate the end effector 60*a* thereof.

Such movement of the decoupling collar 124 of the sterile interface module 100 from the proximal-most position to the distal-most position, imparts forces (e.g., torque) through the respective components of the sterile interface module 100 and the electromechanical surgical instrument 60 to manually manipulate the end effector 60*a* of the electromechanical surgical instrument 60 to position the end effector 60*a* in a desired orientation/position. For example, the end effector

60*a* of the electromechanical surgical instrument 60 can be manually manipulated to an open position to release tissue grasped by the end effector 60*a* so that the electromechanical surgical instrument 60 can be removed from a surgical site while limiting the risks of undesirable tissue damage that would otherwise be present if such manual manipulation were not feasible when a power failure or other similar emergency situation arises. It is also contemplated that the decoupling collar 124 of the sterile interface module 100 can be rotated in the opposite direction as desired to manipulate (e.g., close) the end effector 60*a* of the electromechanical surgical instrument 60.

With the release ring 126 of the sterile interface module 100 removed and the decoupling collar 124 fixed in the distal-most position via the fixed or locking relationship between the tabs 113 and support plate 123 of the sterile interface module 100, the sterile interface module 100 can no longer robotically control any electromechanical surgical instrument coupled thereto such that removal and replacement of the sterile interface module 100 is required. As described above, the sterile interface module 100 can be removed from the robotic surgical assembly 50 by depressing the buttons 72*a*, 72*b* of the sterile interface module 100. A replacement sterile interface module 100 and electromechanical surgical instrument 60 can then be attached as detailed above to enable robotic control of any electrosurgical instrument coupled to the robotic surgical assembly 50 as detailed herein.

Figure 15:
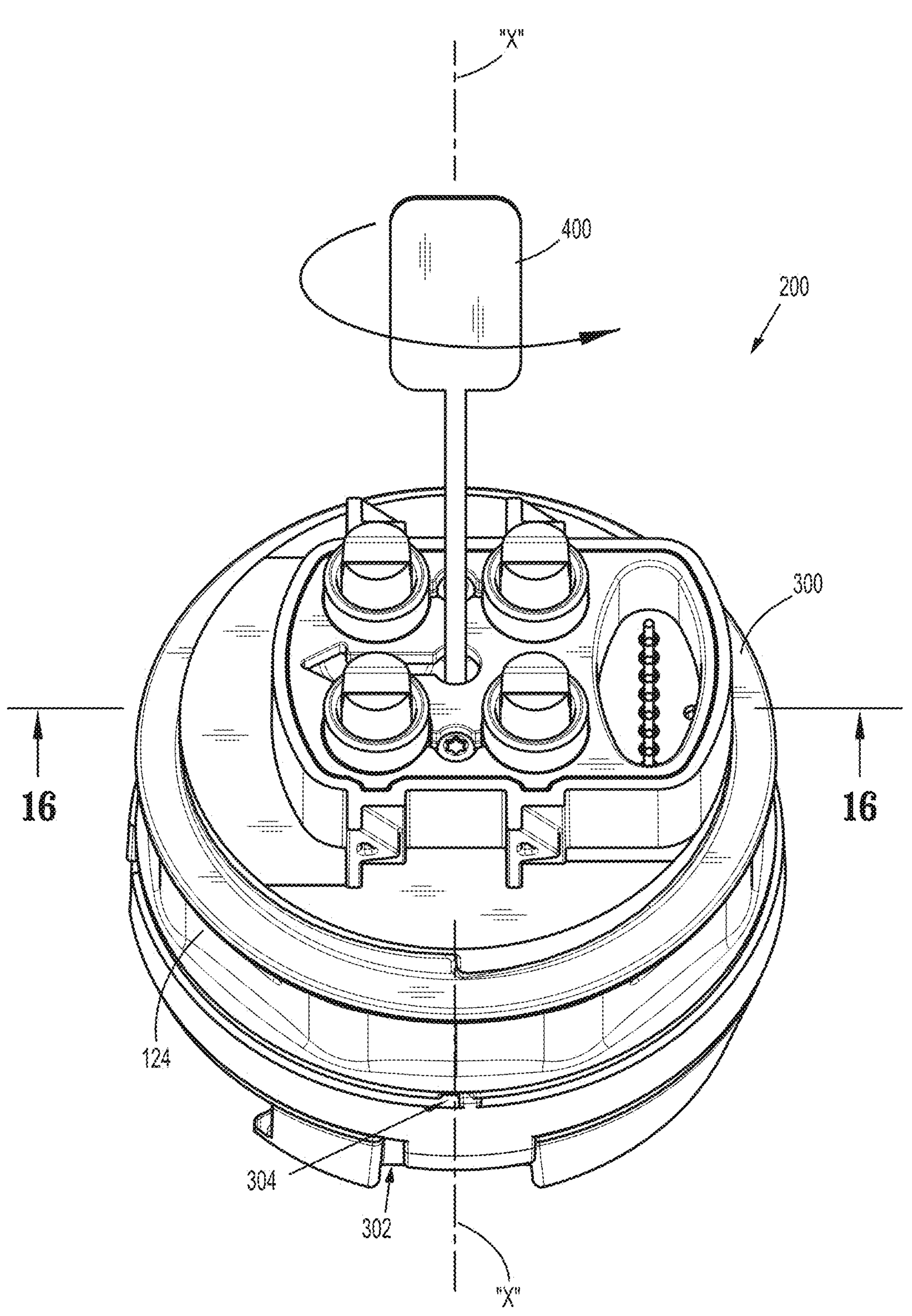
FIG. 15 is a perspective view of one embodiment of a sterile interface module system with a reset tool of the sterile interface module system coupled to a sterile interface module of the sterile interface module system.
Figure 16:
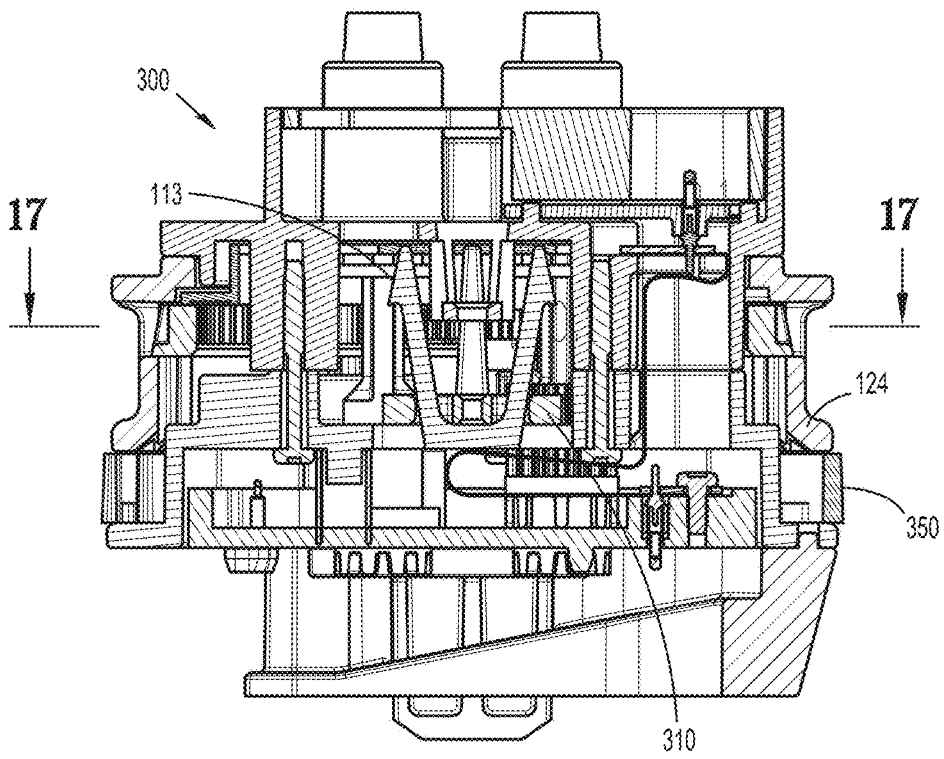
FIG. 16 is a cross-sectional view of the sterile interface module of FIG. 15 as taken along section line 16-16 of FIG. 15.
Figure 17:
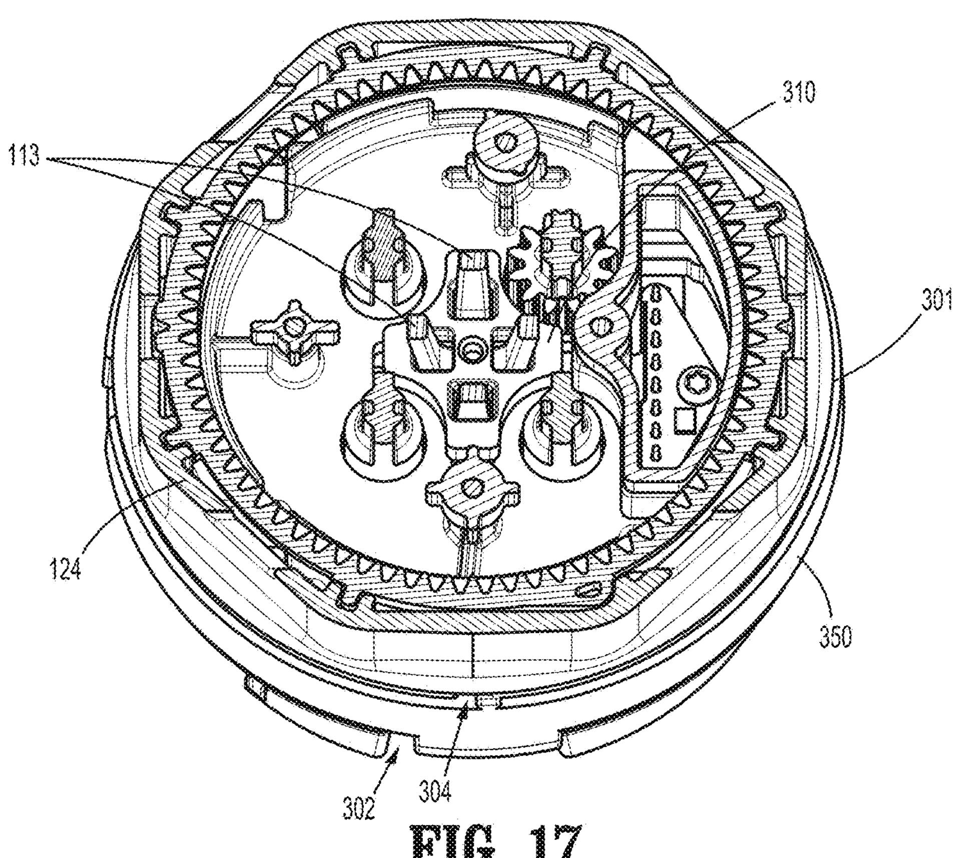
FIG. 17 is a perspective, cross-sectional view of the sterile interface module of FIG. 15 as taken along section line 17-17 of FIG. 16.

Turning now to FIGS. 15-17, one embodiment of sterile interface module system, generally referred to as 200, includes a sterile interface module 300 defining a longitudinal axis "X-X" and a reset tool 400. The sterile interface module 300 is similar to the sterile interface module 100 and includes a body member 301 that supports a reset cam 310 and a release ring 350. The body member 301 of the sterile interface module 300 supports a decoupling collar 124 and includes tabs 113 that cooperate with the reset cam 310. The body member 301 of the sterile interface module 300 defines pull tab recesses 302 and lock slots 304 therein that cooperate with the release ring 350.

Advantageously, the reset tool 400 of the sterile interface module system 200 cooperates with the reset cam 310 of the sterile interface module 300 of the sterile interface module system 200 to enable the sterile interface module 300 to be activated, tested, and reset during the manufacturing assembly and qualification of the sterile interface module 300.

Figures 18, 19A:
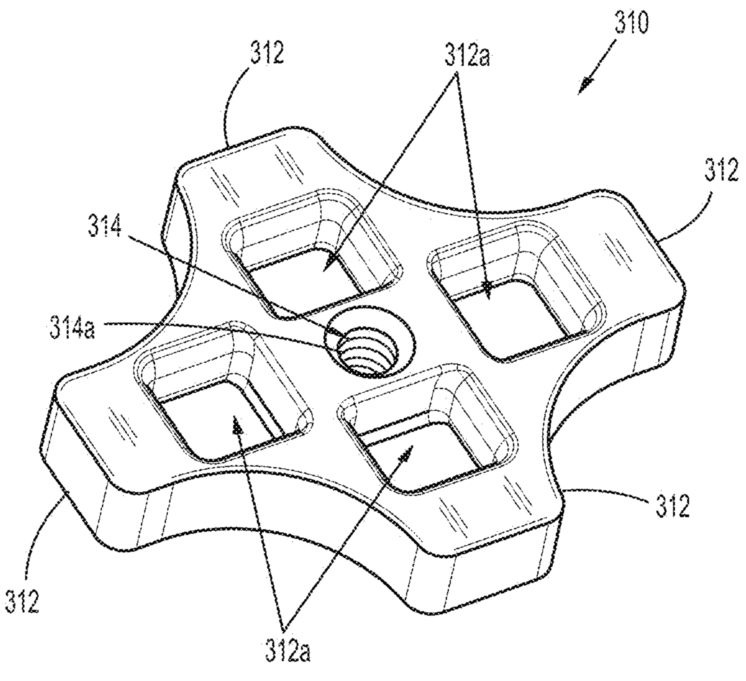
FIG. 18 is a perspective view of a reset cam of the sterile interface module of FIG. 15.
FIGS. 19A-19C are various perspective and top views of a release ring of the sterile interface module of FIG. 15.

As seen in FIGS. 17 and 18, the reset cam 310 of sterile interface module 300 is supported about the tabs 113 of sterile interface module 300 and includes arms 312 that extend radially outward from the reset cam 310 at spaced apart locations about reset cam 310. Each arm 312 of the reset cam 310 defines a receiving aperture 312*a* therethrough that receives a respective one of the tabs 113 of the sterile interface module 300. The reset cam 310 further defines a central opening 314 configured to receive the reset tool 400. The reset cam 310 may include threading 314*a* about central opening 314 to facilitate threaded engagement with reset tool 400. In some embodiments, the reset cam 310 may include a self-tapping feature, boss, and/or a detent feature (not shown) to engage reset tool 400. The reset cam 310 may be formed of any suitable plastic and/or metallic material.

Figure 19B:
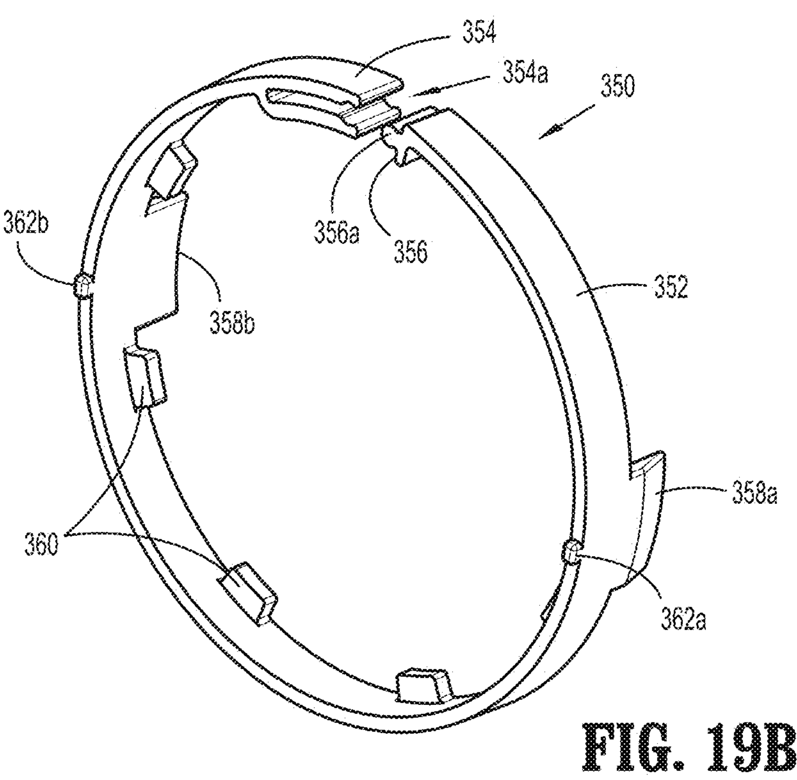
Figure 19C:
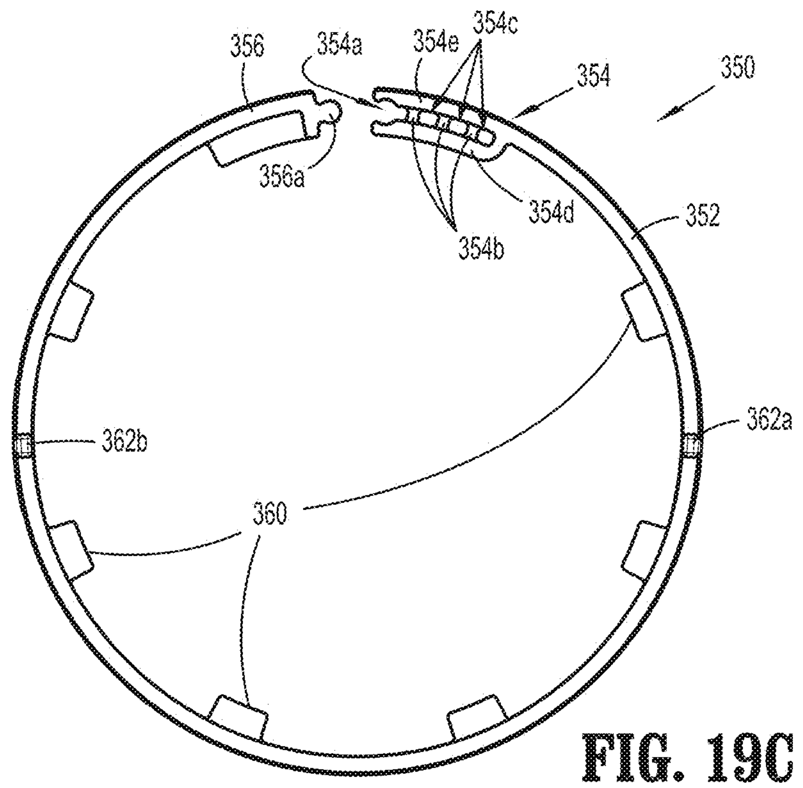

With reference to FIGS. 19A-19C, the release ring 350 of the sterile interface module 300 includes an annular frame 352 having a first end portion 354 and a second end portion 356 that are selectively engagable (e.g., so that release ring 350 is resettable). The annular frame 352 of the release ring 350 supports pull tabs 358*a*, 358*b* on opposed sides of the annular frame 352 (e.g., for ease of access) that extend distally from the annular frame 352 and which include a distal taper configuration that recess pull tabs 358*a*, 358*b* within the pull tab recesses 302 (FIG. 17) of the sterile interface module 300 to help prevent false activation. The pull tabs 358*a*, 358*b* of the release ring 350 may be finger width to provide leverage assist for actuation. An inner surface of the annular frame 352 includes a plurality of radial tabs 360 that extend radially inward to provide concentric alignment with the body member 301 of the sterile interface module 300 and assist in preventing false activation of the release ring 350 from the body member 301 of the sterile interface module 300. A top surface of the annular frame 352 of the release ring 350 supports locking tabs 362*a*, 362*b* that extend proximally therefrom and are aligned with the pull tabs 358*a*, 358*b* of the release ring 350. The locking tabs 362*a*, 362*b* are receivable within the lock slots 304 of the sterile interface module 300. The locking tabs 362*a*, 362*b* function to align the pull tabs 358*a*, 358*b* and to prevent false activation of the release ring 350.

The first end portion 354 of the annular frame 352 of the release ring 350 defines a receiving slot 354*a* and the second end portion 356 of the annular frame 352 includes a protuberance 356*a*. The protuberance 356*a* of the second end portion 356 of the annular frame 352 is receivable within the receiving slot 354*a* of the first end portion 354, for example, via snap-fit, interference-fit or the like to provide optimal separation force for a finger activation, and which can be reset multiple times for disassembly during cleaning, for example.

The first end portion 354 of the annular frame 352 further includes first and second arms 354*d*, 354*e* having spaced-apart tabs 354*b* that extend between the first and second arms 354*d*, 354*e*. The tabs 354*b* define separate openings 354*c* at spaced-apart locations between the first and second arms 354*d*, 354*e* of the first end portion 354. Advantageously, the release ring 350 of the sterile interface module 300 provides a moisture barrier to prevent moisture ingress into the sterile interface module 300. The release ring 350 may be provided in any suitable highly contrasting or bright color, such as orange or red, to help communicate its presence for prompt removal. The release ring 350 can include any suitable indicia such as molded in symbols or text to indicate its purpose as an emergency release. The release ring 350 can be manufactured in any form of a high elongation plastic, elastomer, or flexible material that is conducive for cleaning and sterilization.

Figure 20A:
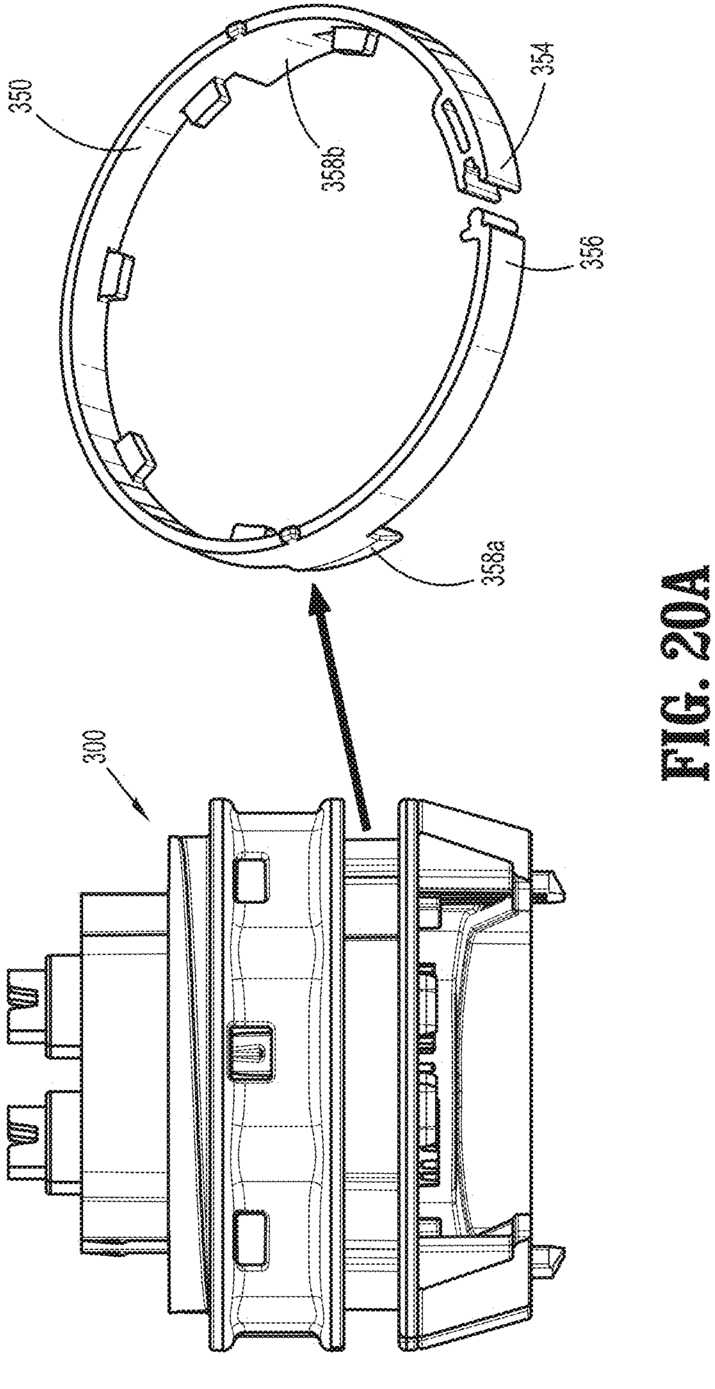
FIGS. 20A-20D are progressive views illustrating operation of the sterile interface module system, including the reset tool of FIG. 15.
Figure 20B:
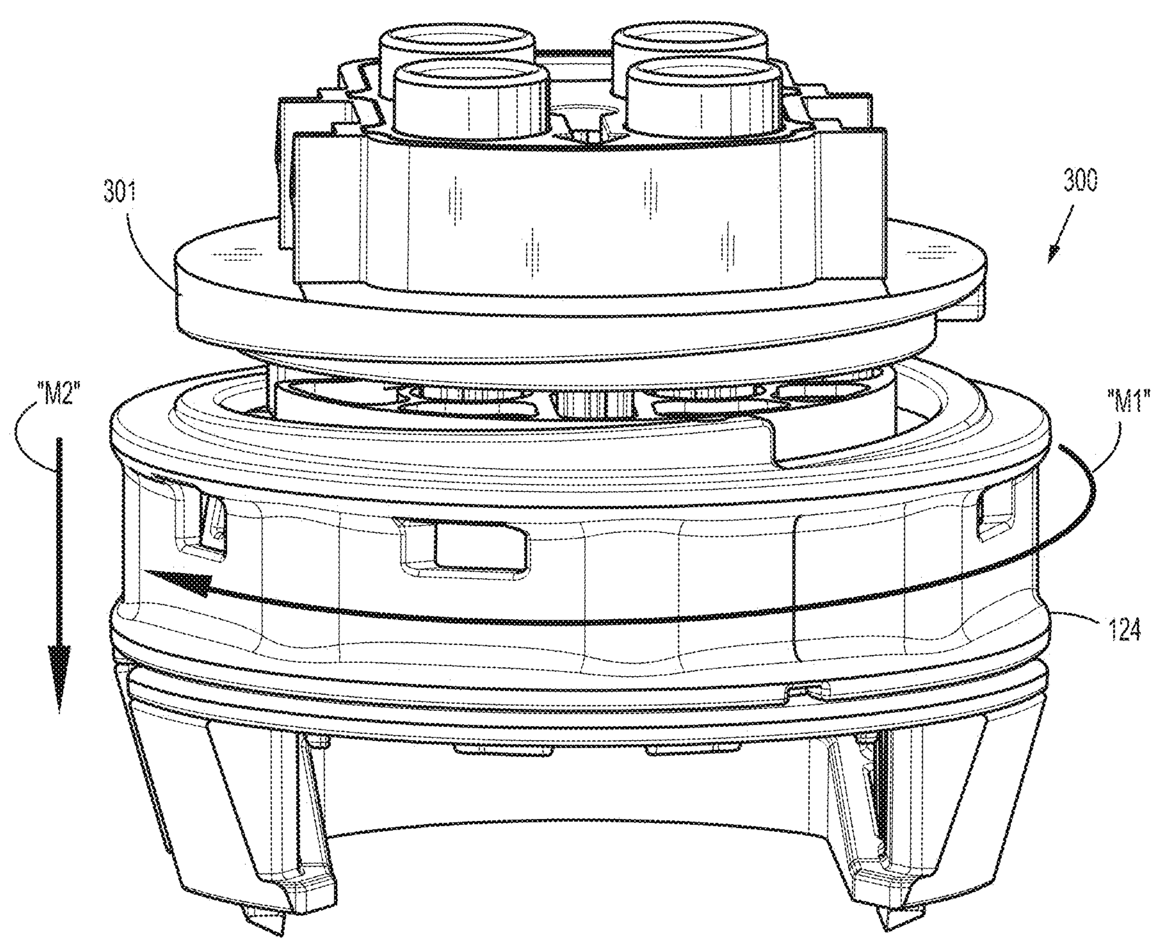

With reference to FIGS. 20A and 20B, in use, the release ring 350 of the sterile interface module 300 is removed by finger actuating one or both of the pull tabs 358*a*, 358*b* of the release ring 350 with sufficient force to separate or uncouple the first and second end portions 354, 356 of the release ring 350 so that the release ring 350 can be unraveled from around the sterile interface module 300 (FIG. 20A). The decoupling collar 124 of the sterile interface module 300 can then be rotated (e.g., counterclockwise) and translated downward about the body member 301 of the sterile interface module 300, as indicated by arrows "M1" and "M2," for example, to test and/or qualify the sterile interface module 300 (FIG. 20B). As the decoupling collar 124 rotates and translates downward, the support plate 123 of the sterile interface module 300 cams along the tabs 113 of the sterile interface module 300 until the tabs 113 extend radially outward over the support plate 123 and prevent the support plate 123 from moving proximally toward its initial position (e.g., lockout the support plate 123).

Figure 20D:
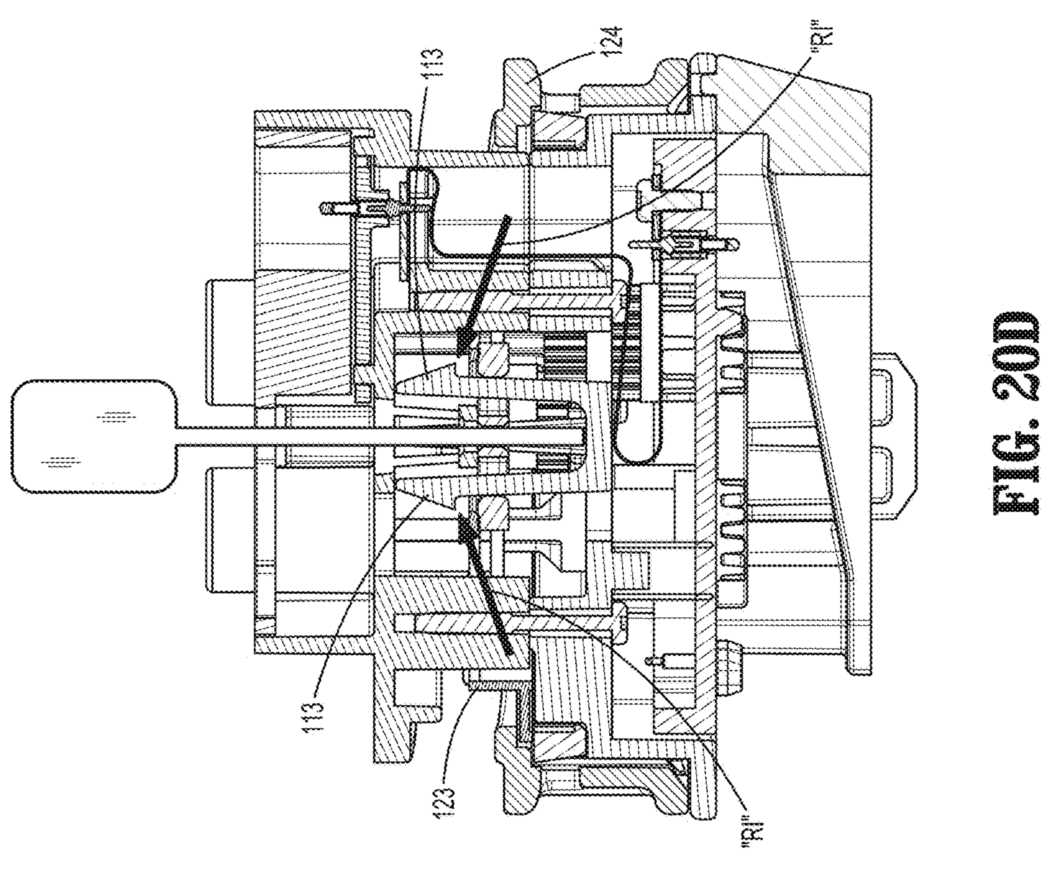
Figure 20C:
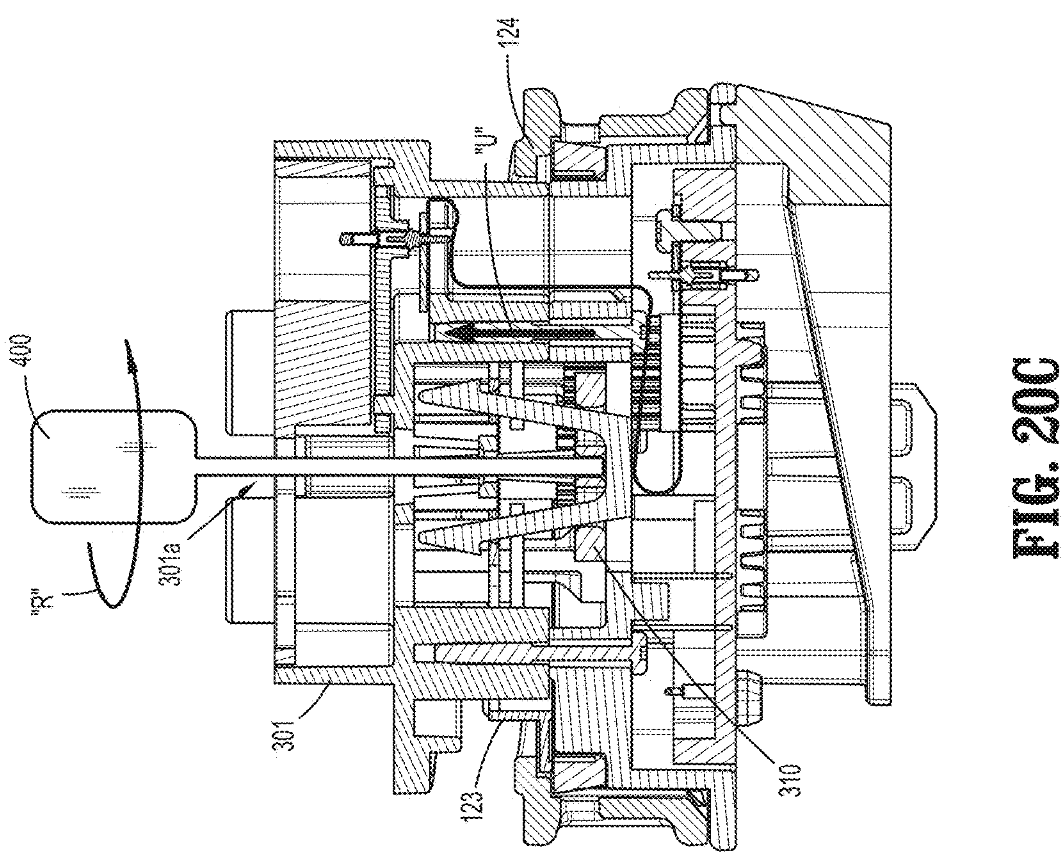

Referring to FIGS. 20C and 20D, to reset the sterile interface module 300, the reset tool 400 can be inserted into a central opening 301*a* defined in the body member 301 of the sterile interface module 300 and advanced into engagement with the reset cam 310. The reset tool 400 can then be manipulated (e.g., rotated) relative to the sterile interface module 300, as indicated by arrows "R," to cause the reset cam 310 to advance axially upwards along the tabs 113 of the body member 301 of the sterile interface module 300, as indicated by arrow "U." As the reset cam 310 cams along the tabs 113, the reset cam 310 approximates the tabs 113 towards one another in a radial inward direction, as indicated by arrows "RI," until the support plate 123 of the sterile interface module 300 can be moved proximally (e.g., translation and/or clockwise rotation of the decoupling collar 124) to its initial proximal position (see FIG. 16) where the support plate 123 is proximal to the tabs 113 of the sterile interface module 300 to reset the sterile interface module 300. Once the support plate 123 is in its proximal position, the reset tool 400 can be removed from the sterile interface module 300. The release ring 350 of the sterile interface module 300, or a new release ring 350, can then be reattached about the body member 301 of the sterile interface module 300 so that the sterile interface module 300 can be used in a surgical procedure.

The robotic surgical system 1 and/or components thereof (e.g., the robotic surgical assembly 50, the sterile interface module 100, 300 etc.) may include one or more electrical components (e.g., electrically coupled to electrical assembly 116*x*) that function to provide sterile interface module identification. For example, these electrical components may include one or more of the following: a contact (which may be an insulated and/or non-insulated contact), a sensor, a magnetic array, a Hall sensor, a Reed switch, a wireless feature, an optical feature, a bar code, a QR code, etc., and/or combinations thereof (not shown), where any of number and/or configuration of each these electrical components may be provided.

Any of the presently disclosed electrical components may function to provide the following for the presently disclosed sterile interface modules and/or as a feed through recognition for a device, instrument, and/or reload unit for one or more of the following: serial number, lot code and/or date code of manufacturing, device type, end of life, calibration date and offsets, reload type, usage and/or number of uses, device status, instrument stroke position, clamp position, wrist position, rotation angle, pitch and/or yaw position, knife and/or cutting mechanism position, energy activation, RF activation, cautery activation, harmonic vibration activation, end effector type, end effector status, end effector position, end effector end of life and/or use status, and/or combinations thereof.

In embodiments, the presently disclosed sterile interface modules can be provided in various configurations, for example, to facilitate manual override functions similar to that described above. For instance, embodiments of sterile interface modules, or components thereof, such as the decoupling collar 124, can be configured to drive and/or operate one or more drives, drive one unique drive, and/or can be rotated clockwise, counterclockwise, and/or combinations thereof. In some embodiments, the decoupling collar 124 can be configured to rotate in a single desired direction.

In certain embodiments, the presently disclosed sterile interface modules, or components thereof (e.g., decoupling collar 124, release ring 126, 350, etc.) can include external ribbing, grooves, texture, etc. to improve manual grasping capability.

In certain embodiments, decoupling one of the presently disclosed sterile interface modules from the drive motor coupler of the instrument drive unit eliminates backdrive loading and reduces the possibility of a seized motor, coupler or gear set or drive within the instrument drive unit.

In some aspects, one failure mode of the instrument drive unit 70 may include a condition in which one or more motors 74*a*, 74*b*, 74*c*, etc. thereof are in a fault state (e.g., cannot applying torque to the drive components of robotic surgical assembly 50 and/or electromechanical surgical instrument 60). In certain aspects, another failure mode may include a condition in which one or more motors 74*a*, 74*b*, 74*c*, etc. of instrument drive unit 70 are unable to rotate. In such aspects, it may be necessary to decouple couplers of the sterile interface module 100 from couplers of the instrument drive unit 70 (e.g., via downward motion) to enable a clinician to spin one or more couplers of the sterile interface module 100 irrespective of a position of corresponding couplers of the instrument drive unit 70. This minimizes the torque needed to rotate the couplers of the sterile interface module 100 by eliminating the need to back drive the motor. Ramp features of the decoupling collar 124 of sterile interface module 100 may aid in such decoupling effort (e.g., the downward motion) and provide a mechanical advantage to lower the force needed to act (e.g., pull down) on the collar 124 by helping provide break-away force needed to overcome initial friction due to engagement of the couplers of robotic surgical assembly 50 and/or electromechanical surgical instrument 60 and the transmission of torque through the interface thereof.

In some embodiments, the decoupling collar may have a diameter that provides large leverage torque for the end user.

In certain embodiments, the presently disclosed sterile interface modules, or components thereof, may include a combination of plastics, or plastics and metals, to eliminate the need for lubrication that can be removed during cleaning and sterilization processes. Plastic materials of the presently disclosed sterile interface module may be produced with high impact and elongation rating plastics that may also be rated for high temperatures and chemical resistance. These materials of the presently disclosed sterile interface module may be specified to provide robust designs for the medical auto washers, autoclave steam sterilization cycling, impact/collisions mild drops and/or abuse during use, and for central processing and cleaning. In some embodiments, materials of the presently disclosed sterile interface module may be high temperature, noncorrosive and/or conducive for autoclaving and/or autowashing. These materials can include, but are not limited to, stainless steel, polyphenylsulfone plastics, PEEK, PPSU (Radel), PSU, PES, Ultem, PAEK, and the like, or combinations thereof. In embodiments, flexible portions of electronics of the presently disclosed sterile interface modules can be mechanically separated, disconnected, or shorted to prevent electronic communication and reuse after activation.

In some embodiments, the presently disclosed sterile interface modules, or components thereof, can include dielectric Insulation, for example, plastics, coatings, films and high dielectric materials can be incorporated to provide a dielectric barrier between the instruments/devices and the instrument drive unit. In certain embodiments, one or more couplers may include a non-conductive plastic to increase the dielectric strength of the interface to coupled devices. In some embodiments, ribs, tongue and grooves, dovetail joints, flanges and/or overlapping walls can be incorporated to increase creepage and clearance dielectric performance.

In some embodiments, the presently disclosed sterile interface modules, or components thereof, can include sealing features. For example, one or more seals can be incorporated to increase fluid resistance and to prevent egress/ingress, one or more seals can be incorporated around the outer diameter of the proximal or distal ends of the couplers, one or more gaskets can be used on the proximal and distal mating faces for sealing, and/or one or more gaskets can be incorporated around the proximal or distal connector interface that compress when mated to the instrument drive unit or instrument.

In certain embodiments, the presently disclosed sterile interface modules, or components thereof, can include side load rail mating features. For example, the presently disclosed sterile interface module, or components thereof, can include lead in features for ease of mating, ribs for locking, dual actuators to prevent false activation, and/or spring loaded plate locking features that lock devices and eliminate play and/or movement of the interface.

In certain embodiments, the presently disclosed sterile interface module, or components thereof, can include one or more wedged surfaces on mounting latches thereof, for example, to eliminate or reduce the mated play/clearances.

In some embodiments, the presently disclosed sterile interface modules, or components thereof, can include cleaning and/or sterilization features. For example, the presently disclosed sterile interface modules, or components thereof, can be configured to be flushable and cleanable to ease cleaning and sterilization. In embodiments, the presently disclosed sterile interface modules, or components thereof, can include a flush port for ease of cleaning. In some embodiments, the presently disclosed sterile interface module, or components thereof, may be disposable and/or adapted for single use.

In embodiments, one or more of the couplers may be Oldham type couplers that allow for full coupling through high levels of tolerance and misalignment. Any of the presently disclosed couplers may include one or more teeth or other similar coupling features.

According to some embodiments, one or more actuators (e.g., two actuators) may be utilized for instrument drive unit mounting to resist false activation during automated usage, collisions, and or by an end user. Actuators may include sub flush, high throw actuators to prevent false actuation.

In some embodiments, one or more couplers can include angular faces that clutch out after attaining a threshold torque. The clutch may be bi directional and/or unidirectional. In embodiments, the clutch torque thresholds can be different values for clockwise and/or counterclockwise rotation.

In some embodiments, the presently disclosed sterile interface modules, or components thereof, can include backlash reduction features. For example, teeth of other similar mating feature of one or more of the couplers may include angled faces which may mate under spring loading. Angled faces may provide ample mating during blind mate conditions and/or can eliminate or reduce backlash when such angled surfaces act as a hard stop for the respective coupler.

In certain embodiments, the presently disclosed sterile interface modules, or components thereof, can include coupler bearings including, but not limited to, integral journal, sleeve, ball, radial, thrust, and/or needle type.

In some embodiments, the presently disclosed sterile interface modules, or components thereof, can include axially floating couplers. For example, axial floating couplers may be configured to float axially on one or both coupling interfaces. Such axial floating couplers may utilize compression, extension, leaf, wave springs and/or elastomers. In embodiments, the floating plate may retain the couplers and act as a thrust bearing surface to simultaneously disengage all couplers in unison.

Mounting features of the presently disclosed sterile interface modules for facilitating mounting thereof may include, but are not limited to, latches, threads, sliders and/or clips.

Electronic features of the presently disclosed sterile interface modules may include coatings and/or potting materials to improve autoclaving and/or autowashing resistance. Such coatings and/or potting materials may include, but are not limited to, humiseal, parylene, and/or silicones. Wires of the electronic features may utilize high temp jacket materials such as Teflon, Teflon blends, and/or silicones. Flex circuit materials of the electronic features may include polyimides for high temperature resistance. These wire and/or flex materials may be provided for a high flex cycle life conduit for the presently disclosed floating interface assemblies.

Figure 21:
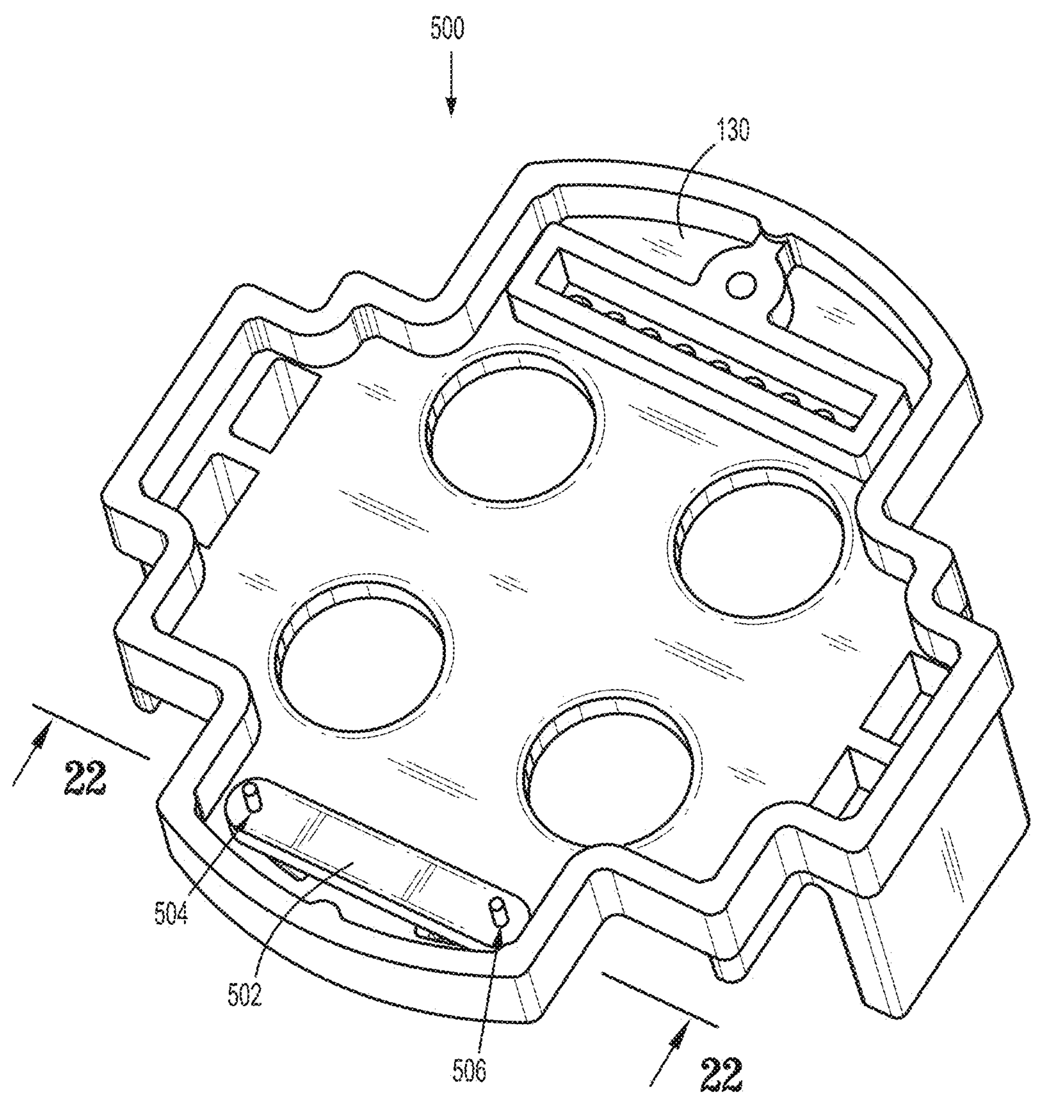
FIG. 21 is a perspective view of one embodiment of a floating plate assembly.
Figure 22:
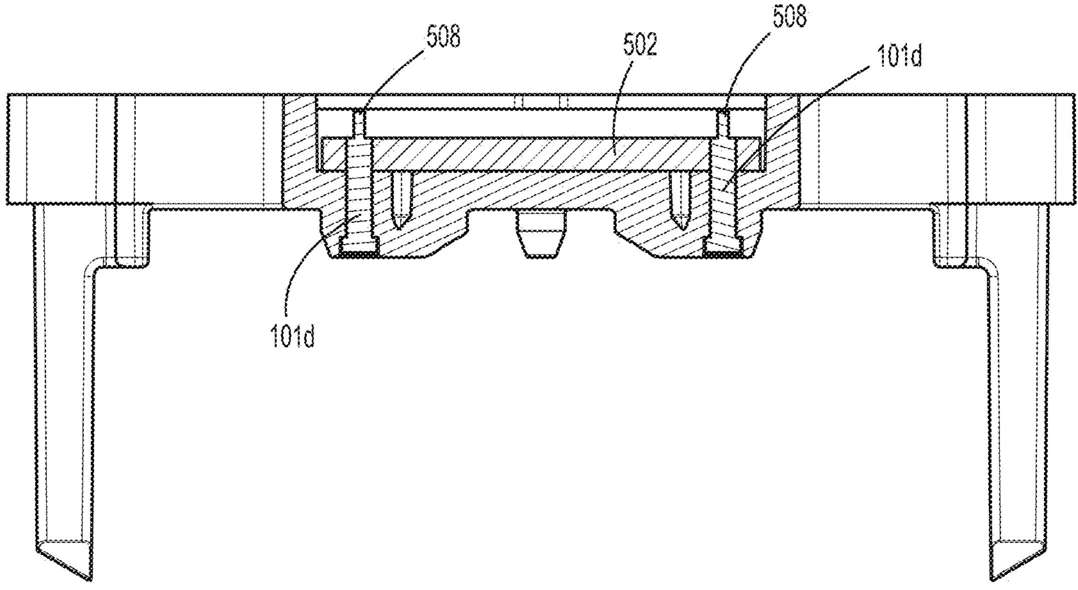
FIG. 22 is a cross-sectional view of the floating plate assembly of FIG. 21 as taken along section line 22-22 shown in FIG. 21.

Turning now to FIGS. 21 and 22, one embodiment of a floating plate assembly, generally referred to as 500, includes the floating plate 130 and a bus bar 502 mounted thereon. The floating plate 130 of the floating plate assembly 500 supports pogo pins **101*d* that are coupled together via the bus bar 502. The bus bar 502 may be in the form of a conductive plate that electrically couples the pogo pins 101*d* and/or mechanically captures or supports the pogo pins 101*d* within the floating plate 130. The bus bar 502 defines spaced-apart openings 504, 506 that receive tips 508 of the pogo pins 101*d* therein. The bus bar 502 may include any suitable flexible material such as a flex printed circuit board (PCB). In some embodiments, the bus bar 502 may include any suitable rigid material such as a rigid PCB. In certain embodiments, the bus bar 502 can be coated with any suitable material such as silicone and/or epoxy. For example, such coating may function to protect the bus bar 502 during an autoclaving and/or cleaning process. In certain embodiments, the bus bar 502 may include metal. The bus bar 502** may have any suitable plating to protect against corrosion.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A sterile interface module for coupling an electromechanical robotic surgical instrument to a robotic surgical assembly, the sterile interface module comprising:

a body member configured to selectively couple the surgical instrument to the robotic surgical assembly;

a decoupling collar supported on the body member and movable relative to the body member from a first position to a second position;

a support plate coupled to the decoupling collar, the support plate having an initial un-used condition and a locked used condition;

a plurality of locking tabs extending from the body member and selectively engageable with the support plate to prevent the decoupling collar from moving from the second position to the first position, the plurality of locking tabs extending away from one another and each locking tab of the plurality of locking tabs terminating in a free end, wherein:

when the support plate is in the initial un-used condition the support plate is not engaged by the plurality of locking tabs, and when the support plate is in the locked used condition the support plate is engaged by the free end of each locking tab of the plurality of locking tabs to prevent return of the support plate to the initial un-used condition; and a reset cam translatably supported about the plurality of locking tabs, wherein as the reset cam translates along the plurality of locking tabs, towards the free ends of the locking tabs, the support plate is free to move from the locked used condition to the initial un-used condition.

2. The sterile interface module of claim 1, wherein the plurality of locking tabs extend through the reset cam.

3. The sterile interface module of claim 2, wherein the plurality of locking tabs are biased radially outward.

4. The sterile interface module of claim 3, further comprising:

a drive transfer assembly supported by the body member and including a drive coupler and a transfer shaft extending from the drive coupler, the drive coupler engagable with the robotic surgical assembly and the transfer shaft engagable with the surgical instrument, the drive coupler configured to engage the robotic surgical assembly while the decoupling collar is in the first position to enable the robotic surgical assembly to robotically control the surgical instrument, the drive coupler retracted within the body member while the decoupling collar is in the second position to prevent the drive coupler from engaging the robotic surgical assembly.

5. The sterile interface module of claim 1, further comprising a release ring supported on the body member and positioned to prevent the decoupling collar from moving from the first position to the second position, the release ring being selectively removable from the body member to enable the decoupling collar to move from the first position to the second position.

6. The sterile interface module of claim 1, wherein the support plate is movable with the decoupling collar.

7. The sterile interface module of claim 1, further comprising an electrical connector supported on the body member and configured to enable electrical communication between the robotic surgical assembly and the surgical instrument.

8. The sterile interface module of claim 7, wherein movement of the decoupling collar from the first position to the second position prevents the electrical connector from providing electrical communication between the robotic surgical assembly and the surgical instrument.

9. The sterile interface module of claim 1, wherein the body member includes a pair of nubs that selectively couple to the robotic surgical assembly to secure the body member to the robotic surgical assembly.

10. The sterile interface module of claim 1, wherein each locking tab of the plurality of locking tabs terminates in a barbed free end.

11. A robotic surgical system, comprising:

a surgical instrument including an end effector;

a robotic surgical assembly; and a sterile interface module supported between the robotic surgical assembly and the surgical instrument to couple the surgical instrument to the robotic surgical assembly, the sterile interface module including:

a body member configured to selectively couple the surgical instrument to the robotic surgical assembly;

a decoupling collar supported on the body member and movable relative to the body member from a first position to a second position;

a support plate coupled to the decoupling collar, the support plate having an initial un-used condition and a locked used condition;

a plurality of locking tabs extending from the body member and selectively engageable with the support plate to prevent the decoupling collar from moving from the second position to the first position, the plurality of locking tabs extending away from one another and each locking tab of the plurality of locking tabs terminating in a free end, wherein:

when the support plate is in the initial un-used condition the support plate is not engaged by the plurality of locking tabs, and when the support plate is in the locked used condition the support plate is engaged by the free end of each locking tab of the plurality of locking tabs to prevent return of the support plate to the initial un-used condition; and a reset cam translatably supported about the plurality of locking tabs, wherein as the reset cam translates along the locking tabs, towards the free ends of the locking tabs, the support plate is free to move from the locked used condition to the initial un-used condition.

12. The robotic surgical system of claim 11, wherein the plurality of locking tabs extend through the reset cam.

13. The robotic surgical system of claim 12, wherein the plurality of locking tabs are biased radially outward.

14. The robotic surgical system of claim 13, further comprising:

a drive transfer assembly supported by the body member and including a drive coupler and a transfer shaft extending from the drive coupler, the drive coupler engageable with the robotic surgical assembly and the transfer shaft engageable with the surgical instrument, the drive coupler configured to engage the robotic surgical assembly while the decoupling collar is in the first position to enable the robotic surgical assembly to robotically control the surgical instrument, the drive coupler retracted within the body member while the decoupling collar is in the second position to prevent the drive coupler from engaging the robotic surgical assembly.

15. The robotic surgical system of claim 11, wherein the support plate is movable with the decoupling collar.

16. The robotic surgical system of claim 11, further comprising a release ring supported on the body member and positioned to prevent the decoupling collar from moving from the first position to the second position, the release ring being selectively removable from the body member to enable the decoupling collar to move from the first position to the second position.

17. The robotic surgical system of claim 11, further comprising an electrical connector supported on the body member and configured to enable electrical communication between the robotic surgical assembly and the surgical instrument.

18. The robotic surgical system of claim 17, wherein movement of the decoupling collar from the first position to the second position prevents the electrical connector from providing electrical communication between the robotic surgical assembly and the surgical instrument.

19. The robotic surgical system of claim 17, wherein the electrical connector is recessed within the body member.

20. The robotic surgical system of claim 11, wherein the sterile interface module includes nubs that selectively couple to the robotic surgical assembly to secure the sterile interface module to the robotic surgical assembly, and wherein the robotic surgical assembly includes buttons that face in the same direction and are depressible to decouple the nubs of the sterile interface module from the robotic surgical assembly so that the sterile interface module releases from the robotic surgical assembly.

* * * * *